US009451882B2

(12) United States Patent
Nie et al.

(10) Patent No.: US 9,451,882 B2
(45) Date of Patent: Sep. 27, 2016

(54) INTEGRATED SYSTEM AND METHODS FOR REAL-TIME ANATOMICAL GUIDANCE IN A DIAGNOSTIC OR THERAPEUTIC PROCEDURE

(71) Applicant: Emory University, Atlanta, GA (US)

(72) Inventors: Shuming Nie, Atlanta, GA (US); Aaron Mohs, Atlanta, GA (US); Michael Mancini, Atlanta, GA (US)

(73) Assignee: EMORY UNIVERSITY, Atlanta, GA (US)

( * ) Notice: Subject to any disclaimer, the term of this patent is extended or adjusted under 35 U.S.C. 154(b) by 0 days.

(21) Appl. No.: 14/086,334

(22) Filed: Nov. 21, 2013

(65) Prior Publication Data
US 2014/0081133 A1 Mar. 20, 2014

Related U.S. Application Data

(63) Continuation of application No. 12/969,396, filed on Dec. 15, 2010, now abandoned.

(60) Provisional application No. 61/286,519, filed on Dec. 15, 2009, provisional application No. 61/385,613, filed on Sep. 23, 2010.

(51) Int. Cl.
*A61B 5/00* (2006.01)
*A61B 5/06* (2006.01)
(Continued)

(52) U.S. Cl.
CPC ........... *A61B 5/0035* (2013.01); *A61B 5/0071* (2013.01); *A61B 5/0075* (2013.01);
(Continued)

(58) Field of Classification Search
CPC A61B 5/0071; A61B 5/0075; A61B 5/0077; A61B 5/0086; A61K 49/0017
See application file for complete search history.

(56) References Cited

U.S. PATENT DOCUMENTS 5,261,410 A 11/1993 Alfano et al.
5,715,836 A 2/1998 Kliegis et al.
(Continued)

FOREIGN PATENT DOCUMENTS

JP H09-000497 A 1/1997
JP 11-004898 1/1999
(Continued)

OTHER PUBLICATIONS

Abigail S. Haka et al., Diagnosing breast cancer by using Raman spectroscopy, PNAS, Aug. 30, 2005, pp. 12371-12376, vol. 102, No. 35.
(Continued)

*Primary Examiner* — Serkan Akar
(74) *Attorney, Agent, or Firm* — Sutherland Asbill & Brennan LLP

(57) ABSTRACT

According to one aspect, a system for intraoperatively providing anatomical guidance in a diagnostic or therapeutic procedure is disclosed. In one embodiment, the system includes: a first light source configured to emit a beam of visible light; second light source configured to emit a beam of near-infrared light; a handheld probe optically coupled to the second light source; a second imaging device configured to detect visible light; a third imaging device configured to detect near-infrared light having a first predetermined wavelength; a fourth imaging device configured to detect near-infrared light having a second predetermined wavelength; a display for displaying at least one visual representation of data; and, a controller programmed to generate at least one real-time integrated visual representation of an area of interest and to display the real-time visual representation on the display for guidance during the diagnostic or therapeutic procedure.

27 Claims, 19 Drawing Sheets

(51) Int. Cl.
*A61B 19/00* (2006.01)
*A61K 49/00* (2006.01)

(52) U.S. Cl.
CPC ............... *A61B5/0077* (2013.01); *A61B 5/06* (2013.01); *A61B 5/415* (2013.01); *A61B 5/418* (2013.01); *A61B 5/7425* (2013.01); *A61B 19/5225* (2013.01); *A61K 49/0017* (2013.01); *A61B 5/0086* (2013.01)

(56) References Cited

U.S. PATENT DOCUMENTS

| | | | |
|---|---|---|---|
| 5,740,802 | A | 4/1998 | Nafis et al. |
| 5,772,593 | A | 6/1998 | Hakamata |
| 6,317,616 | B1 | 11/2001 | Glossop |
| 6,748,259 | B1 | 6/2004 | Benaron et al. |
| 7,182,166 | B2 | 2/2007 | Gray et al. |
| 2002/0013531 | A1 | 1/2002 | Hayashi |
| 2002/0062061 | A1 | 5/2002 | Kaneko et al. |
| 2002/0103439 | A1 | 8/2002 | Zeng et al. |
| 2002/0173723 | A1 | 11/2002 | Lewis et al. |
| 2004/0006276 | A1 | 1/2004 | Demos et al. |
| 2004/0073120 | A1 | 4/2004 | Motz et al. |
| 2004/0236229 | A1 | 11/2004 | Freeman et al. |
| 2005/0143662 | A1 | 6/2005 | Marchitto et al. |
| 2005/0182321 | A1 | 8/2005 | Frangioni |
| 2006/0155195 | A1 | 7/2006 | Maier et al. |
| 2006/0184040 | A1* | 8/2006 | Keller et al. ................ 600/476 |
| 2006/0258942 | A1 | 11/2006 | Van Beek et al. |
| 2007/0153268 | A1 | 7/2007 | Panza et al. |
| 2007/0167836 | A1 | 7/2007 | Scepanovic et al. |
| 2008/0051629 | A1 | 2/2008 | Sugiyama et al. |
| 2008/0058629 | A1 | 3/2008 | Seibel et al. |
| 2008/0267472 | A1 | 10/2008 | Demos |
| 2009/0024018 | A1 | 1/2009 | Boyden et al. |
| 2009/0236541 | A1* | 9/2009 | Lomnes et al. ............ 250/458.1 |
| 2010/0145200 | A1* | 6/2010 | Mahadevan-Jansen et al. ............................ 600/476 |
| 2011/0104071 | A1 | 5/2011 | Lee et al. |
| 2011/0152692 | A1 | 6/2011 | Nie et al. |
| 2012/0123205 | A1 | 5/2012 | Nie et al. |

FOREIGN PATENT DOCUMENTS

| | | |
|---|---|---|
| JP | 11-104059 | 4/1999 |
| JP | 2000-206047 A | 7/2000 |
| JP | 2004-089533 A | 3/2004 |
| JP | 2004-520105 A | 7/2004 |
| JP | 2004520105 A | 7/2004 |
| JP | 2004-294099 A | 10/2004 |
| JP | 2006180926 | 7/2006 |
| JP | 2009-125411 A | 6/2009 |
| JP | 2009-133876 A | 6/2009 |
| WO | 02/50518 A2 | 6/2002 |
| WO | 2009/028136 A1 | 3/2009 |

OTHER PUBLICATIONS

Abigail S. Haka et al., In vivo margin Assessment during Partial Mastectomy Breast Surgery Using Raman Spectroscopy, Cancer Research, Mar. 15, 2006, pp. 3317-3322, vol. 66, No. 6.

Andrew I. Minchinton et al., Drug penetration in solid tumours, Nature Reviews Cancer, Aug. 2006, pp. 583-592, vol. 6.

C. Gebitekin et al., Fate of patients with residual tumour at the bronchial resection margin, European Journal of Cardia-thoracic Surgery, 1994, pp. 339-343, vol. 8.

Elizabeth M. Kanter, PDS et al., Effect of hormonal variation on Raman spectra for cervical disease detection, American Journal of Obstetrics & Gynecology, May 2009, pp. 512.e1-512.e5, 200.

John P. Neoptolemos et al., Influence of Resection Margins on Survival for patients With Pancreatic Cancer Treated by Adjuvant Chemoradiation and/or Chemotherapy in the ESPAC-1 Randomized Controlled Trial, Annals of Surgery, 2001, pp. 758-768, vol. 234, No. 6.

Markus G. Muller, PHD et al., Spectroscopic Detection and Evaluation of Morphologic and Biochemical Changes in Early Human Oral Carcinoma, American Cancer Society, Apr. 1, 2003, pp. 1681-1692, vol. 97, No. 7.

Matthew R. Dreher et al., Tumor Vascular Permeability, Accumulation, and Penetration of Macromolecular Drug Carriers, Journal of the National Cancer Institute, Mar. 1, 2006, pp. 335-344, vol. 98, No. 5.

Rakesh K. Jain, Transport of Molecules, particles, and Cells in Solid Tumors, Annu. Rev. Biomed. Eng., 1999, pp. 241-263, vol. 1.

Sanjiv Sam Gambhir, Molecularimaging of Cancer with Positron Emission Tomography, Nature Reviews Cancer, Sep. 2002, pp. 683-693, vol. 2.

Susan L. Troyan, MD et al., The Flare Intraoperative near-Infrared Fluorescence Imaging System: A First-in-Human Clinical Trial in Breast Cancer Sentinel Lymph Node Mapping, Annals of Surgical Oncology, Society of Surgical Oncology, 2009.

Tami Karni, M.D. et al., A device for real-time, intraoperative margin assessment in breast-conservation surgery, The American Journal of Surgery, 2007, pp. 467-473, vol. 194.

Xiaohu Gao et al., In vivo cancer targeting and imaging with semiconductor quantum dots, Nature Biotechnology, Aug. 2004, pp. 969-976, vol. 22, No. 8.

PCT International Search Report and Written Opinion for International Application No. PCT/US2014/063923 dated Apr. 24, 2015.

English Translation of Japanese Office Action mailed Sep. 9, 2015 for patent application No. JP 2012-544798.

* cited by examiner

INTEGRATED SYSTEM AND METHODS FOR REAL-TIME ANATOMICAL GUIDANCE IN A DIAGNOSTIC OR THERAPEUTIC PROCEDURE

CROSS-REFERENCE TO RELATED PATENT APPLICATIONS

This application is a continuation patent application of U.S. patent application Ser. No. 12/969,396, filed Dec. 15, 2010 and published Jun. 23, 2011 as U.S. Patent Appl. Publication No. 2011/0152692, now abandoned, which claims the benefit, pursuant to 35 U.S.C. §119(e), of provisional U.S. Patent Application Ser. No. 61/286,519, filed Dec. 15, 2009 and now expired, entitled "SYSTEM AND METHODS FOR INTRAOPERATIVELY PROVIDING ANATOMICAL GUIDANCE IN A SURICAL PROCEDURE," by Shuming Nie, Aaron Mohs, and Michael Mancini, and provisional U.S. Patent Application Ser. No. 61/385,613, filed Sep. 23, 2010 and now expired, entitled "A HANDHELD SPECTROSCOPIC DEVICE FOR IN VIVO AND INTRA-OPERATIVE TUMOR DETECTION: CONTRAST ENHANCEMENT, DETECTION SENSITIVITY, AND TISSUE PENETRATION," by Shuming Nie, Aaron Mohs, and Michael Mancini, the disclosures of which are herein incorporated by reference in their entireties.

STATEMENT OF FEDERALLY-SPONSORED RESEARCH

This invention was made with Government support under Grant No. U54CA011933 awarded by the National Institutes of Health. The Government has certain rights in the invention.

Some references, which may include patents, patent applications and various publications, are cited and discussed in the description of this invention. The citation and/or discussion of such references is provided merely to clarify the description of the present invention and is not an admission that any such reference is "prior art" to the invention described herein. All references cited and discussed in this specification are incorporated herein by reference in their entireties and to the same extent as if each reference was individually incorporated by reference. In terms of notation, hereinafter, "[n]" represents the nth reference cited in the reference list. For example, [4] represents the 4$^{th}$ reference cited in the reference list, namely, Karakiewicz, P. I. et al., *Urology* 2005, 66, 1245-1250.

FIELD OF THE INVENTION

The present invention generally relates to systems and methods for intraoperatively providing guidance in a diagnostic or therapeutic procedure.

BACKGROUND OF THE INVENTION

Many forms of human cancer are treated by surgical resection, chemotherapy, and/or radiation. Surgery provides significant survival advantages for a broad range of tumor types and cures approximately 45% of all patients with solid tumors [1]. To successfully treat a patient with surgery, the surgeon must remove the entire tumor at the time of surgery including the primary tumor, draining lymph nodes that may contain tumor cells and small adjacent satellite nodules. Statistical data indicate that complete resection is the single most important predictor of patient survival for almost all solid tumors [2]. In lung, breast, prostate, colon, and pancreatic cancers, a complete resection has a 3-5 fold improvement in survival as compared to partial resection [3-8]. Recent advances in computed tomography (CT), positron emission tomography (PET), and hybrid techniques (such as CT/PET) have greatly improved tumor detection and surgical planning [9,10], but these modalities do not provide real-time intra-operative assistance. Intra-operative magnetic resonance imaging (MRI) can assist in surgical resection of tumors, but it is time consuming and substantially adds to the length of surgery, anesthesia time, and financial costs [11]. Intra-operative sonography has also shown potential for detection of breast cancer but has limited sensitivity for detection of masses less than 5 mm [12]. Faced with these difficulties, optical technologies based on cellular imaging, native fluorescence, and Raman scattering have gained attention for tumor detection and diagnosis [13-17]. In particular, the level of autofluorescence from collagen, nicotinamide adenine dinucleotide (NADH), and flavin adenine dinucleotide (FAD) has been associated with malignancy in head and neck cancer [17-19]. Chemical and biochemical changes have been measured by laser Raman spectroscopy for margin assessment of breast cancer [15, 20] and for noninvasive detection of cervical dysplasia during routine pelvic exams [21]. Small changes in cellular biochemistry may translate into spectroscopic differences that are measurable with fluorescence or Raman scattering. However, tumors are highly heterogeneous in their molecular and cellular compositions [22], and biochemical differences in malignant and benign tissues are subject to natural variations in patient physiology and pathology [23]. Thus, autofluorescence and intrinsic Raman measurements often lead to unacceptable false-positive rates for benign tissues and unacceptable false-negative rates for malignant tissues [24, 25].

Due to tissue scattering and blood absorption, optical methods have relatively limited penetration depths [26, 27]. For intra-operative applications, however, the lesions are surgically exposed and can be brought in close proximity to the imaging device, so they become accessible to optical illumination and detection. A problem in using exogenous contrast agents is that they are often unable to deeply penetrate solid tumors, especially when macromolecules such as monoclonal antibodies or nanoparticles are used [28-30]. For detection of tumor margins during surgery, on the other hand, the agents are detected at the tumor periphery and deep penetration is not required. Similarly, for detection of small and residual tumors, deep penetration is not required because small tumors do not have a high intra-tumoral pressure or a necrotic/hypoxic core, two factors in limiting tumor penetration of imaging and therapeutic agents [28-30].

There is a need for anatomical guidance and rapid pathology to be provided during the diagnostic or therapeutic procedure, to determine if a tumor has been completely resected, such as by verifying that the margin of resected tumor tissue is clear, without having to wait for pathology to process the resected tissue to verify that there are no remaining signs of cancerous growth in the margin.

Therefore, a heretofore unaddressed need still exists in the art to address the aforementioned deficiencies and inadequacies.

SUMMARY OF THE INVENTION

In one aspect, the present invention relates to a system for intraoperatively providing anatomical guidance in a diagnostic or therapeutic procedure. In one embodiment, the system includes a first light source that is configured to emit a beam of visible light to an area of interest of a living subject and a second light source that is configured to emit a beam of near-infrared light to the area of interest. The system also includes a handheld probe that is optically coupled to the second light source that includes an optical fiber configured to deliver the emitted beam of near-infrared light to illuminate the area of interest. The optical fiber is also configured to collect light that is scattered or light that is emitted from a contrast agent introduced into target tissues in the area of interest in response to illumination by the second light source. A first imaging device is also included in the system. The first imaging device is optically coupled to the handheld probe and is configured to detect the collected light and to generate a corresponding signal that includes collected light data. The handheld probe is further configured to transmit the collected light to the first imaging device, through the optical fiber. The system further includes a second imaging device that is configured to detect visible light that is emitted from the area of interest in response to illumination by the first light source, and to generate a corresponding signal including visible light data. A third imaging device is also included in the system, which is configured to detect near-infrared light having a first predetermined wavelength that is emitted from the area of interest, in response to illumination by the second light source, and which is also configured to generate a corresponding signal including a first set of near-infrared light data. In addition, the system includes a fourth imaging device that is configured to detect near-infrared light having a second predetermined wavelength that is different from the first predetermined wavelength and that is emitted from the area of interest, in response to illumination by the second light source, and the fourth imaging device is also configured to generate a corresponding signal that includes a second set of near-infrared light data. A display for displaying at least one visual representation of data is further included in the system. Also, the system includes a controller that is in communication with each of the first light source, second light source, first imaging device, second imaging device, third imaging device, fourth imaging device, and display. The controller may include one or more programmable processors that are operative to cause a computer to perform specific functions. In this embodiment, the controller is programmed to generate at least one real-time integrated visual representation of the area of interest from each of the collected light data, visible light data, first set of near-infrared light data, and second set of near-infrared light data, and to display the real-time visual representation on the display for guidance during the diagnostic or therapeutic procedure.

In one embodiment, the contrast agent includes a Raman probe and/or a fluorescence probe and the collected light data includes Raman data and/or fluorescence data, respectively. In this embodiment, the integrated visual representation includes a wide-field image of the area of interest that is generated from the visible light data, a laser excitation image of a selected area of the area of interest that is defined within the wide-field image and that is generated from at least one of the generated first set of near-infrared light data and the generated second set of near-infrared light data, and a Raman image generated from the Raman data and/or a fluorescence image generated from the fluorescence data. The Raman image and/or fluorescence image is defined within the wide-field image and the laser excitation image, as an overlay image on the laser excitation image.

In one embodiment, the first imaging device includes a spectrometer and each of the second imaging device, third imaging device, and fourth imaging device includes a CCD camera.

In another aspect, the present invention relates to an imaging system using integrated bright-field imaging, near-infrared imaging, and Raman imaging and/or fluorescence imaging for intraoperatively evaluating target tissues in an area of interest of a living subject. In one embodiment, the system includes a first light source for delivering a beam of visible light to the area of interest and a second light source for delivering a beam of near-infrared light to the area of interest. The system also includes a Raman and/or fluorescence imaging means that includes a handheld probe optically coupled to the second light source, for delivering the near infrared light to illuminate target tissues of the area of interest, and for collecting scattered light and/or emitted light from a corresponding Raman probe and/or fluorescence probe that is introduced into the target tissues and illuminated by the second light source. The system further includes a first imaging device that is in communication with the handheld probe, for obtaining Raman data and/or fluorescence data from the collected light. In this embodiment, the first imaging device includes a spectrometer. A bright-field imaging means is also included in the system according to this embodiment. The bright-field imaging means includes: an optical port; a system lens including a UV-NIR compact lens and a first achromatic correction lens; a silver mirror; a first dichroic mirror and a second dichroic mirror; a first shortpass filter and a second shortpass filter; a neutral density filter; a bandpass filter; a longpass filter; a second achromatic lens, a third achromatic lens, and a fourth achromatic lens; a second imaging device for obtaining visible light data from visible light emitted from the area of interest in response to illumination by the first light source; a third imaging device for obtaining a first set of near-infrared data from light having a first predetermined wavelength that is emitted from the area of interest in response to illumination by the second light source; and, a fourth imaging device for obtaining a second set of near infrared data from light having a second predetermined wavelength that is different from the first predetermined wavelength and that is emitted from the area of interest in response to illumination by the second light source. Each of the second imaging device, third imaging device, and fourth imaging device include a CCD camera.

In one embodiment, the optical port and the first imaging device define a first optical path between them that includes the silver mirror, the first dichroic mirror, the second dichroic mirror, and the second achromatic lens, where the optical port and the second imaging device define a second optical path between them that includes the silver mirror, first dichroic mirror, second dichroic mirror, neutral density filter, and third achromatic lens. The optical port and the third imaging device define a third optical path between them that includes the silver mirror, first dichroic mirror, longpass filter, bandpass filter, and fourth achromatic lens. The system according to this embodiment also includes a display for displaying at least one visual representation of data, and a controller in communication with each of the first light source, second light source, first imaging device, second imaging device, third imaging device, fourth imaging device, and display. The controller may include one or more programmable processors that are operative to cause a computer to perform specific functions. In this embodiment, the controller is programmed for generating in real time an integrated visual representation of the area of interest from the collected light data, first set of near-infrared data, second set of near-infrared data, and displaying the integrated visual representation on the display, to provide guidance for performing a diagnostic or therapeutic procedure.

In one embodiment, the real-time integrated visual representation of the area of interest includes a wide-field image of the area of interest generated from the visible light data, a laser excitation image of a predetermined area defined within the wide-field image that is generated from the first set of near-infrared data and/or the second set of near-infrared data, and a Raman image and/or fluorescence image that is defined within the laser excitation image and that is generated from corresponding Raman data and/or fluorescence data. The Raman image and/or fluorescence image is an overlay image on the laser excitation image.

In one embodiment, the integrated visual representation of the area of interest includes a wide-field image of the area of interest generated from the visible light data, a laser excitation image of a predetermined area defined within the wide-field image that is generated from at lest one of the first set of near-infrared data and the second set of near-infrared data, and at least one of a Raman image and a fluorescence image that is generated from a corresponding at least one of the Raman data and fluorescence data. The laser excitation image is an overlay image on the wide-field image and represents the location of the delivered beam of near-infrared light within the area of interest. The Raman data and/or fluorescence data is represented by a signal that, when exceeding a predefined threshold level, signifies disease in the target tissues.

Further, the Raman image and/or the fluorescence image is a color overlay image on the laser excitation image, having an opacity representative of the level of the signal exceeding the predefined threshold level, and the opacity of the color overlay image decays over time to be progressively more translucent relative to the laser excitation image.

In yet another aspect, the present invention relates to a method for intraoperatively providing anatomical guidance in a diagnostic or therapeutic procedure. In one embodiment, the method includes the steps of introducing at least one contrast agent into target tissues in an area of interest of a living subject, and the step of emitting a beam of visible light to the area of interest, using a first light source. The method also includes the step of emitting a beam of near-infrared light to the area of interest, using a second light source, and the step of delivering the emitted beam of near-infrared light to illuminate the area of interest, using an optical fiber of a handheld probe that is optically coupled to the second light source. In addition, the method includes the step of collecting scattered light and/or emitted light from the contrast agent in response to illumination by the second light source, using the optical fiber of the handheld probe. The contrast agent includes a Raman probe and/or a fluorescence probe. Further, the method includes the step of detecting the collected light and generating a corresponding signal that includes collected light data, using a first imaging device that is optically coupled to the optical fiber. The optical fiber is further configured to deliver the collected light to the first imaging device. The method also includes the step of detecting visible light that is emitted from the area of interest in response to illumination by the first light source and generating a corresponding signal comprising visible light data, using a second imaging device, and the step of detecting near-infrared light having a first predetermined wavelength that is emitted from the area of interest in response to illumination by the second light source and generating a corresponding signal that includes a first set of near-infrared light data, using a third imaging device. Still further, the method includes the step of detecting near-infrared light having a second predetermined wavelength that is different from the first predetermined wavelength and that is emitted from the area of interest in response to illumination by the second light source, and generating a corresponding signal that includes a second set of near-infrared light data, using a fourth imaging device, and the step of generating at least one real-time integrated visual representation of the area of interest from the collected light data, visible light data, first set of near-infrared data, and second set of near-infrared data, using a controller that is in communication with each of the first imaging device, second imaging device, third imaging device, and fourth imaging device. The controller may include one or more programmable processors that are operative to cause a computer to perform operational steps according to the method. In this embodiment, the method also includes the step of displaying the real-time integrated visual representation generated by the controller, for guidance during a surgical procedure, using a display that is in communication with the controller.

In one embodiment, the step of generating the real-time integrated visual representation of the area of interest includes the steps of generating a wide-field image of the area of interest from the visible light data, generating a laser excitation image of a selected area of the area of interest that is defined within the wide-field image, from the first set of near-infrared light data and/or the second set of near-infrared light data, and generating a Raman image and/or a fluorescence image from the collected light data that is defined within the wide-field image and the laser excitation image. The Raman image and/or fluorescence image is an overlay image on the laser excitation image.

In one embodiment, the first imaging device includes a spectrometer, and each of the second imaging device, third imaging device, and fourth imaging device includes a CCD camera.

In yet another aspect, the present invention relates to a computer-readable medium having stored, computer-executable instructions which, when executed by a controller, cause a computer to perform specific functions. In one embodiment, the controller is programmed for causing a computer to perform functions for intraoperatively providing anatomical guidance in a diagnostic or therapeutic procedure. The controller may include one or more programmable processors. In one embodiment, the functions include causing a first light source in communication with the controller to emit a beam of visible light to an area of interest of a living subject, causing a second light source optically coupled to an optical fiber and in communication with the controller to emit a beam of near-infrared light to the area of interest through the optical fiber, and causing the optical fiber of the handheld probe to collect light scattered from a Raman probe and/or light emitted from fluorescence probe, in response to illumination by the second light source. The Raman probe and/or fluorescence probe is introduced into the target tissues in the area of interest. The functions also include causing a first imaging device that is in communication with the controller and the optical fiber to detect the collected light, and causing the first imaging device to generate a signal from the collected light that includes Raman data and/or fluorescence data.

Further, the functions include causing a second imaging device that is in communication with the controller to detect visible light that is emitted from the area of interest in response to illumination by the first light source, causing the second imaging device to generate a corresponding signal comprising visible light data, causing a third imaging device that is in communication with the controller to detect near-infrared light having a first predetermined wavelength that is emitted from the area of interest in response to illumination by the second light source, and causing the third imaging device to generate a corresponding signal that includes a first set of near-infrared light data.

In addition, the functions include causing a fourth imaging device that is in communication with the controller to detect near-infrared light having a second predetermined wavelength that is different from the first predetermined wavelength and that is emitted from the area of interest in response to illumination by the second light source, and causing the fourth imaging device to generate a corresponding signal that includes a second set of near-infrared light data. Further, the functions include generating at least one real-time integrated visual representation of the area of interest from the visible light data, first set of near-infrared data, second set of near-infrared data, and from the Raman data and/or fluorescence data, and causing a display in communication with the controller to display the generated real-time integrated visual representation for guidance during a surgical procedure.

In one embodiment, the function of generating the real-time integrated visual representation of the area of interest includes the steps of generating a wide-field image of the area of interest from the visible light data, generating a laser excitation image of a selected area of the area of interest that is defined within the wide-field image from the first set near-infrared light data and/or the second set of near-infrared light data, and generating a Raman image from the Raman data and/or a fluorescence image from the fluorescence data, that is defined within the wide-field image and the laser excitation image.

In one embodiment, the Raman image and/or fluorescence image is an overlay image on the laser excitation image. The first imaging device includes a spectrometer, and each of the second imaging device, third imaging device, and fourth imaging device includes a CCD camera.

In yet another aspect, the present invention relates to a method for intraoperatively identifying disease in target tissues in an area of interest of a living subject, to be resected in a diagnostic or therapeutic procedure. In one embodiment, the method includes the step of introducing a Raman probe and/or a fluorescence probe into the area of interest until the probe has accumulated in the target tissues, the step of preparing the living subject and the area of interest for a surgical procedure, and the step of initializing an imaging system for integrated bright-field imaging, near-infrared imaging, and Raman imaging and/or fluorescence imaging. The method also includes the step of beginning the diagnostic or therapeutic procedure in the area of interest, the step of using a first real-time integrated visual representation of the area of interest and the target tissues that is generated by the imaging system to identify a boundary of the target tissues that are diseased, and the step of performing a surgical resection of the identified diseased target tissues within the boundary. Further, the method includes the steps of, after the surgical resection, using a second displayed real-time integrated visual representation of the area of interest and the target tissues, generated by the imaging system, to identify any remaining diseased target tissues within the boundary and, if any remaining diseased target tissues are identified, performing a series of further surgical resections on identified remaining diseased target tissues corresponding to a respective series of real-time integrated visual representations generated by the imaging system, until the area of interest is free from diseased target tissues.

In one embodiment, the imaging system includes a first light source that is configured to emit a beam of visible light to an area of interest of a living subject and a second light source that is configured to emit a beam of near-infrared light to the area of interest. The system also includes a handheld probe that is optically coupled to the second light source, and that includes an optical fiber that is configured to deliver the emitted beam of near-infrared light to illuminate the area of interest and that is also configured to collect light that is scattered or light that is emitted from a contrast agent introduced into target tissues in the area of interest, in response to illumination by the second light source. A first imaging device is also included in the system. The first imaging device is optically coupled to the handheld probe and is configured to detect the collected light and to generate a corresponding signal that includes collected light data. The handheld probe is further configured to transmit the collected light to the first imaging device through the optical fiber. The system further includes a second imaging device that is configured to detect visible light that is emitted from the area of interest in response to illumination by the first light source, and to generate a corresponding signal including visible light data. A third imaging device is also included in the system, which is configured to detect near-infrared light having a first predetermined wavelength that is emitted from the area of interest, in response to illumination by the second light source, and which is also configured to generate a corresponding signal including a first set of near-infrared light data. In addition, the system includes a fourth imaging device that is configured to detect near-infrared light having a second predetermined wavelength that is different from the first predetermined wavelength, and that is emitted from the area of interest in response to illumination by the second light source. The fourth imaging device is also configured to generate a corresponding signal that includes a second set of near-infrared light data. A display for displaying at least one visual representation of data is further included in the system. Also, the system includes a controller that is in communication with each of the first light source, second light source, first imaging device, second imaging device, third imaging device, fourth imaging device, and display. The controller may include one or more processors that are programmed to cause a computer to perform specific functions. The controller is programmed to generate at least one real-time integrated visual representation of the area of interest from each of the collected light data, visible light data, first set of near-infrared light data, and second set of near-infrared light data, and to display the at least one real-time visual representation on the display for guidance during the diagnostic or therapeutic procedure.

In one embodiment of the method, each of the steps of identifying diseased target tissues from the displayed visual representation includes identifying visual representations of the emitted laser excitation light and visual representations of the collected light data that are displayed in a selected area of the visual representation.

In one embodiment, the step of identifying the boundary of the target tissues that are diseased and the step of identifying any remaining diseased target tissues within the boundary includes identifying visual representations of the first set of near-infrared light data, second set of near-infrared light data, and collected light data that are displayed in a selected area of the integrated visual representation. The visual representation of the first set of near-infrared data and second set of near-infrared data is a laser excitation image that represents the location of the delivered beam of near-infrared light within the area of interest, and that is displayed as a color overlay image on the wide-field image.

The signal representing the collected light data that is generated by the first imaging device, when exceeding a predetermined threshold level, signifies disease in the target tissues. The visual representation of the collected light data is a color overlay image on the laser excitation image, having an opacity representative of the level of the signal exceeding the predefined threshold level. The opacity of the color overlay image that represents the collected light data decays over time to be progressively more translucent relative to the laser excitation image.

These and other aspects of the present invention will become apparent from the following description of the preferred embodiments, taken in conjunction with the following drawings, although variations and modifications therein may be affected without departing from the spirit and scope of the novel concepts of the disclosure.

BRIEF DESCRIPTION OF THE DRAWINGS

The patent or application filed contains at least one drawing executed in color. Copies of this patent or patent application publication with color drawing(s) will be provided by the Office upon request and payment of the necessary fee.

The accompanying drawings illustrate one or more embodiments of the invention and, together with the written description, serve to explain the principles of the invention. Wherever possible, the same reference numbers are used throughout the drawings to refer to the same or like elements of an embodiment, and wherein.

DEFINITIONS

Figure 1A:
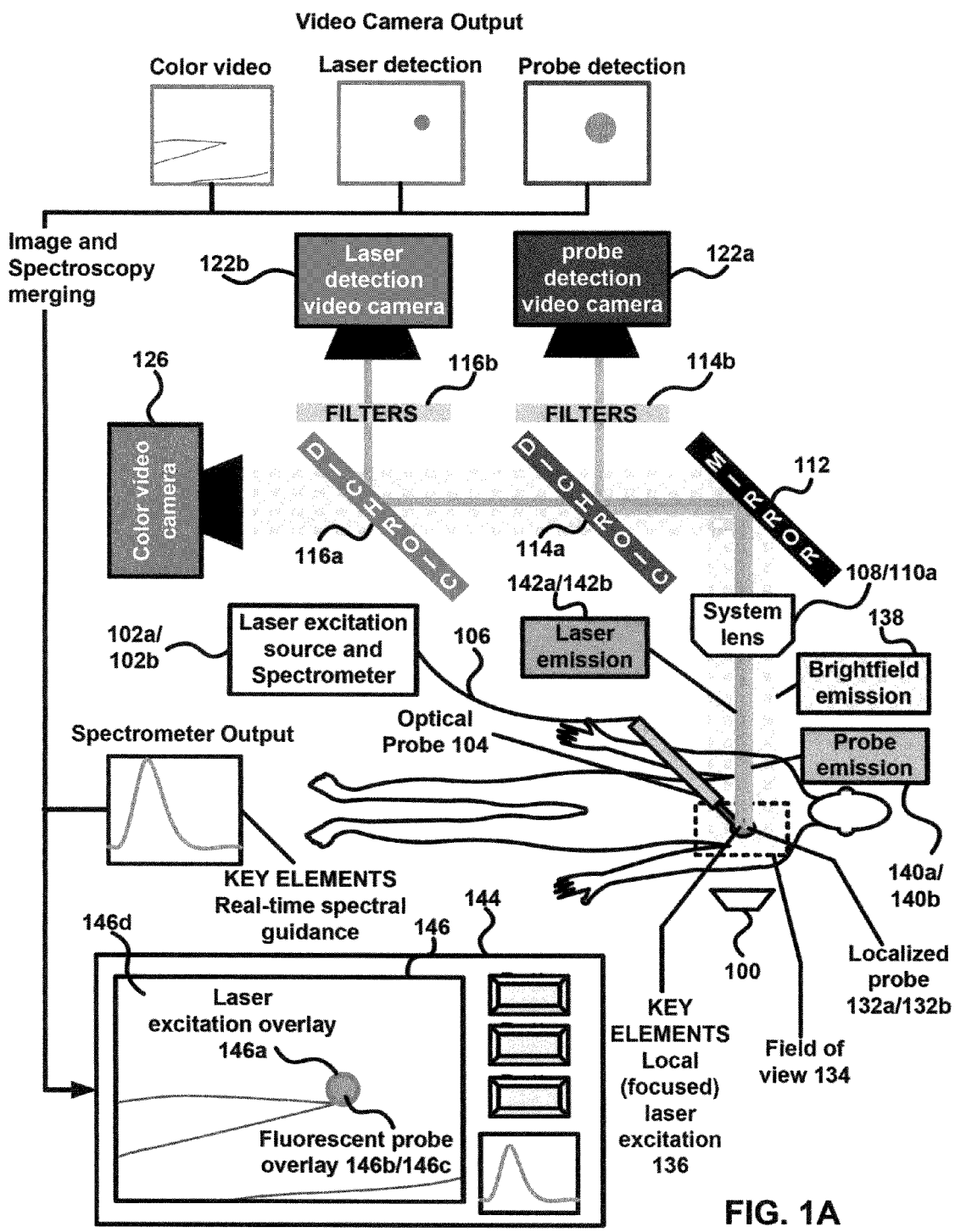
FIG. 1A schematically shows a system for intraoperatively providing anatomical guidance in a diagnostic or therapeutic procedure, according to one embodiment of the present invention.

The terms used in this specification generally have their ordinary meanings in the art, within the context of the invention, and in the specific context where each term is used.

Certain teens that are used to describe the invention are discussed below, or elsewhere in the specification, to provide additional guidance to the practitioner in describing the apparatus and methods of the invention and how to make and use them. For convenience, certain terms may be highlighted, for example using italics and/or quotation marks. The use of highlighting has no influence on the scope and meaning of a term; the scope and meaning of a term is the same, in the same context, whether or not it is highlighted. It will be appreciated that the same thing can be said in more than one way. Consequently, alternative language and synonyms may be used for any one or more of the terms discussed herein, nor is any special significance to be placed upon whether or not a term is elaborated or discussed herein. Synonyms for certain terms are provided. A recital of one or more synonyms does not exclude the use of other synonyms. The use of examples anywhere in this specification, including examples of any terms discussed herein, is illustrative only, and in no way limits the scope and meaning of the invention or of any exemplified term. Likewise, the invention is not limited to various embodiments given in this specification. Furthermore, subtitles may be used to help a reader of the specification to read through the specification, which the usage of subtitles, however, has no influence on the scope of the invention.

OVERVIEW OF THE INVENTION

The present invention is more particularly described in the following examples that are intended as illustrative only since numerous modifications and variations therein will be apparent to those skilled in the art. Various embodiments of the invention are now described in detail. Referring to the drawings, like numbers indicate like components throughout the views. As used in the description herein and throughout the claims that follow, the meaning of "a", "an", and "the" includes plural reference unless the context clearly dictates otherwise. Also, as used in the description herein and throughout the claims that follow, the meaning of "in" includes "in" and "on" unless the context clearly dictates otherwise.

The description will be made as to the embodiments of the present invention in conjunction with the accompanying drawings in FIGS. 1-13.

Figure 1B:
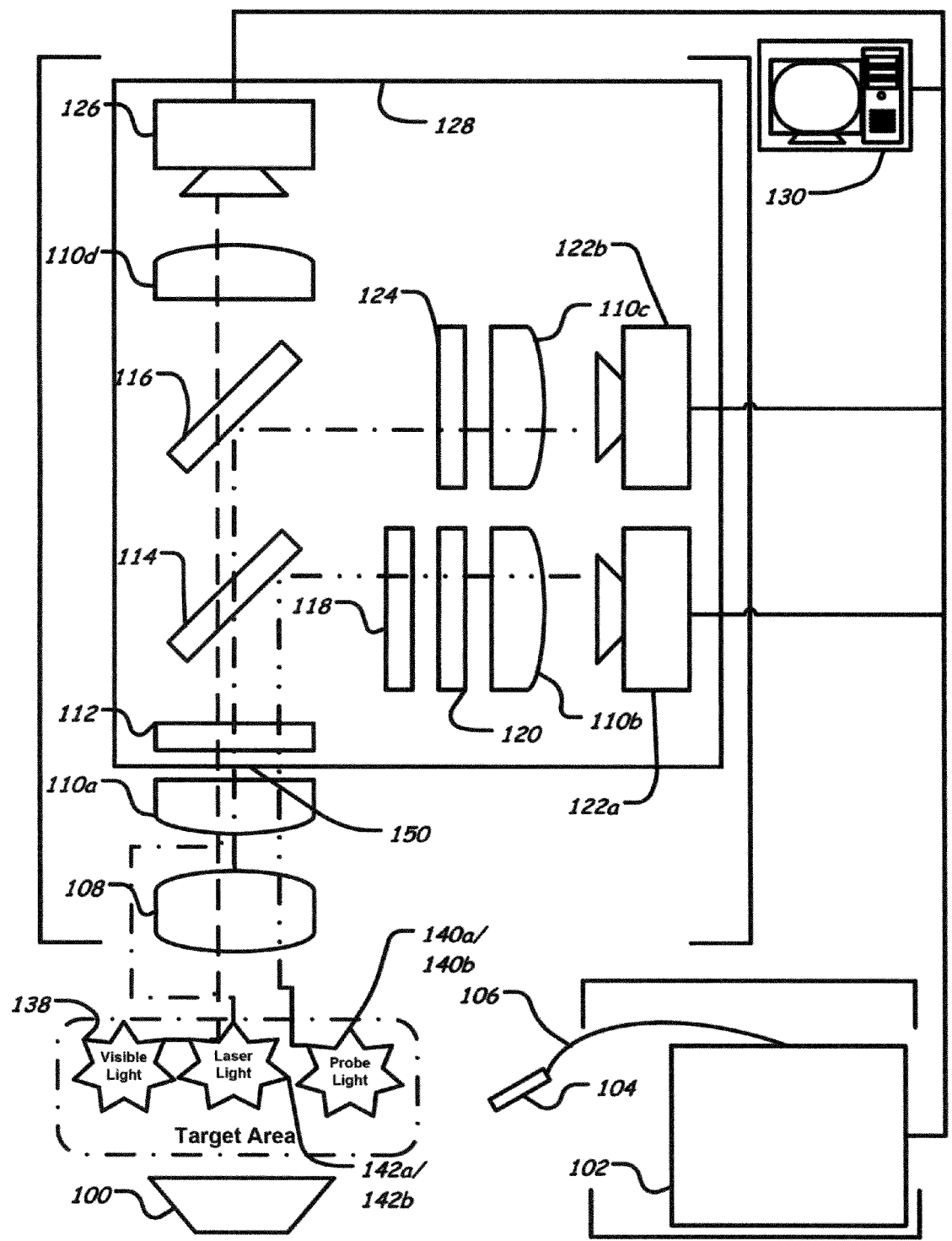
FIG. 1B schematically shows another view of the system according to the embodiment shown in FIG. 1A.

Now referring to FIGS. 1A and 1B, in one aspect, the present invention relates to a system for intraoperatively providing anatomical guidance in a surgical procedure. In one embodiment, the system includes a first light source 100 that is configured to emit a beam of visible light to an area of interest 134 of a living subject, and a second light source 102a that is configured to emit a beam of near-infrared light to the area of interest 134. The system also includes a handheld probe 104 that is optically coupled to the second light source 102a and that includes an optical fiber 106 configured to deliver the emitted beam of near-infrared light to illuminate the area of interest 134. The optical fiber 106 and is also configured to collect light that is scattered 140a and/or or light that is emitted 140b from a contrast agent 132a/132b introduced into target tissues in the area of interest 134, in response to illumination by the second light source 102a. A first imaging device 102b is also included in the system. The first imaging device 102b is optically coupled to the handheld probe 104 and is configured to detect the collected light 140a/140b and to generate a corresponding signal that includes collected light data. The handheld probe 104 is further configured to transmit the collected light 140a/140b to the first imaging device 102b through the optical fiber 106. The system further includes a second imaging device 126 that is configured to detect visible light 138 that is emitted from the area of interest 134 in response to illumination by the first light source 100, and to generate a corresponding signal that includes visible light data. A third imaging device 122a is also included in the system, which is configured to detect near-infrared light 142a having a first predetermined wavelength that is emitted from the area of interest 134, in response to illumination by the second light source 102a, and which is also configured to generate a corresponding signal that includes a first set of near-infrared light data. In addition, the system includes a fourth imaging device 122b that is configured to detect near-infrared light 142b having a second predetermined wavelength that is different from the first predetermined wavelength and that is emitted from the area of interest 134, in response to illumination by the second light source 102a. The fourth imaging device 122b is also configured to generate a corresponding signal that includes a second set of near-infrared light data. A display 144 for displaying at least one visual representation of data is further included in the system. Also, the system includes a controller 130 that is in communication with each of the first light source 100, second light source 102a, first imaging device 102b, second imaging device 126, third imaging device 122a, fourth imaging device 122b, and display 144. The controller 130 may include one or more programmable processors that are operative to cause a computer to perform specific functions. The controller 130 is programmed to generate at least one real-time integrated visual representation 146 of the area of interest 134 from each of the collected light data, visible light data, first set of near-infrared light data, and second set of near-infrared light data, and to display the visual representation on the display 144 for guidance during the surgical procedure.

In one embodiment, the contrast agent 132a/132b includes a Raman probe 132a and/or a fluorescence probe 132b and the collected light data includes Raman data and/or fluorescence data, respectively. In this embodiment, the integrated visual representation 146 includes a wide-field image 146d of the area of interest 134 that is generated from the visible light data, and a laser excitation image 146a of a selected area of the area of interest 134 that is defined within the wide-field image 146d. The laser excitation image 146a and that is generated from at least one of the generated first set of near-infrared light data and the generated second set of near-infrared light data, and from a Raman image 146b generated from the Raman data and/or a fluorescence image 146c generated from the fluorescence data. The Raman image 146b and/or fluorescence image 146c is defined within the wide-field image 146d and the laser excitation image 146a, as an overlay image on the laser excitation image 146a.

In one embodiment, the first imaging device 102b includes a spectrometer and each of the second imaging device 126, third imaging device 122a, and fourth imaging device 122b includes a CCD camera.

In another aspect, the present invention relates to an imaging system using integrated bright-field imaging, near-infrared imaging, and Raman imaging and/or fluorescence imaging, for intraoperatively evaluating target tissues in an area of interest 134 of a living subject. In one embodiment, the system includes a first light source 100 for delivering a beam of visible light to the area of interest 134 and a second light source 102a for delivering a beam of near-infrared light to the area of interest 134. The system also includes a Raman imaging means and/or fluorescence imaging means that includes a handheld probe 104 optically coupled to the second light source 102a, for delivering the near infrared light to illuminate target tissues of the area of interest 134, and for collecting scattered light 140a and/or emitted light 140b from a corresponding Raman probe 132a and/or fluorescence probe 132b that is introduced into the target tissues and illuminated by the second light source 102a. The system further includes a first imaging device 102b that is in communication with the handheld probe 104, for obtaining Raman data and/or fluorescence data from the collected light 140a/140b. In this embodiment, the first imaging device 102b includes a spectrometer.

A bright-field imaging means is also included in the system according to this embodiment. The bright-field imaging means includes: an optical port 150; a system lens 108/110a including a UV-NIR compact lens 108 and a first achromatic correction lens 110a; a silver mirror 112; a first dichroic mirror 114a and a second dichroic mirror 116a; a first shortpass filter 114b and a second shortpass filter 116b; a neutral density filter 124; a bandpass filter 120; a longpass filter 118; a second achromatic lens 110b, a third achromatic lens 110c, and a fourth achromatic lens 110d; a second imaging device 126 for obtaining visible light data from visible light 138 emitted from the area of interest 134 in response to illumination by the first light source 100; a third imaging device 122a for obtaining a first set of near-infrared data from light 142a having a first predetermined wavelength that is emitted from the area of interest 134 in response to illumination by the second light source 102a; and, a fourth imaging device 122b for obtaining a second set of near infrared data from light 142b having a second predetermined wavelength that is different from the first predetermined wavelength and that is emitted from the area of interest 134 in response to illumination by the second light source 102a. Each of the second imaging device 126, third imaging device 122a, and fourth imaging device 122b includes a CCD camera.

In one embodiment, the optical port 150 and the second imaging device 102b define a first optical path between them that includes the silver mirror 112, the first dichroic mirror 114a, the second dichroic mirror 116a, and the second achromatic lens 110b. The optical port 150 and the fourth imaging device 126 define a second optical path between them that includes the silver mirror 112, first dichroic mirror 114a, second dichroic mirror 116a, neutral density filter 124, and third achromatic lens 110c. The optical port 150 and the third imaging device 122a define a third optical path between them that includes the silver mirror 112, first dichroic mirror 114a, longpass filter 118, bandpass filter 120, and fourth achromatic lens 110d. The system of this embodiment also includes a display 144 for displaying at least one visual representation 146 of data, and a controller 130 in communication with each of the first light source 100, second light source 102a, first imaging device 102b, second imaging device 126, third imaging device 122a, fourth imaging device 122b, and display 144. The controller may include one or more processors operative to cause a computer to perform specific functions. The controller 130 is programmed for generating in real time an integrated visual representation 146 of the area of interest 134 from the collected light data, visible light data, first set of near-infrared data, and second set of near-infrared data. The controller 130 is also programmed for displaying the integrated visual representation 146 on the display 144, to provide guidance for performing a surgical procedure.

In one embodiment, the real-time integrated visual representation 146 of the area of interest 134 includes a wide-field image 146d of the area of interest 134 that is generated from the visible light data, a laser excitation image 146a of a predetermined area defined within the wide-field image 146d that is generated from the first set of near-infrared data and/or the second set of near-infrared data, and a Raman image 146b and/or fluorescence image 146c that is defined within the laser excitation image 146a and that is generated from corresponding Raman data and/or fluorescence data. The Raman image 146b and/or fluorescence image 146e is an overlay image on the laser excitation image 146a.

In yet another aspect, the present invention relates to a method for intraoperatively providing anatomical guidance in a surgical procedure. In one embodiment, the method includes the steps of introducing at least one contrast agent 132a/132b into target tissues in an area of interest 134 of a living subject, and the step of emitting a beam of visible light to the area of interest 134, using a first light source 100. The method also includes the step of emitting a beam of near-infrared light to the area of interest 134, using a second light source 102a, and the step of delivering the emitted beam of near-infrared light to illuminate the area of interest 134, using an optical fiber 106 of a handheld probe 104 that is optically coupled to the second light source 102a. In addition, the method includes the step of collecting scattered light 140a and/or emitted light 140b from the contrast agent 132a/132b in response to illumination by the second light source 102a, using the optical fiber 106 of the handheld probe 104. The contrast agent 132a/132b includes a Raman probe 132a and/or fluorescence probe 132b. Further, the method includes the step of detecting the collected light 140a/140b and generating a corresponding signal that includes collected light data, using a first imaging device 102b optically coupled to the optical fiber 106. The optical fiber 106 is further configured to deliver the collected light 140a/140b to the first imaging device 102b.

The method also includes the step of detecting visible light 138 that is emitted from the area of interest 134 in response to illumination by the first light source 100 and generating a corresponding signal that includes visible light data, using a second imaging device 126. Further, the method includes the step of detecting near-infrared light 142a having a first predetermined wavelength that is emitted from the area of interest 134 in response to illumination by the second light source 102a and generating a corresponding signal that includes a first set of near-infrared light data, using a third imaging device 122a. Still further, the method includes the step of detecting near-infrared light 142b having a second predetermined wavelength that is different from the first predetermined wavelength and that is emitted from the area of interest 134 in response to illumination by the second light source, and generating a corresponding signal including a second set of near-infrared light data, using a fourth imaging device 122b. In addition, the method includes the step of generating at least one real-time integrated visual representation 146 of the area of interest 134 from the collected light data, visible light data, first set of near-infrared data, and second set of near-infrared data, using a controller 130 that is in communication with each of the first imaging device 102b, second imaging device 126, third imaging device 122a, and fourth imaging device 122b. The method further includes the step of displaying the real-time integrated visual representation 146 generated by the controller 130, for guidance during a surgical procedure, using a display 144 that is in communication with the controller 130. The controller 130 may include one or more processors that are operative to cause a computer to perform specific functions.

In one embodiment, the step of generating the real-time integrated visual representation 146 of the area of interest 134 includes the steps of generating a wide-field image 146d of the area of interest 134 from the visible light data, generating a laser excitation image 146a of a selected area of the area of interest 134 that is defined within the wide-field image 146d, from the first set of near-infrared light data and/or the second set of near-infrared light data, and generating a Raman image 140a and/or a fluorescence image 140b from the collected light data, that is defined within the wide-field image 146d and the laser excitation image 146a. The Raman image 140a and/or fluorescence image 140b is an overlay image on the laser excitation image 146a.

In one embodiment, the first imaging device 102b includes a spectrometer, and each of the second imaging device 126, third imaging device 122a, and fourth imaging device 122b includes a CCD camera.

In yet another aspect, the present invention relates to a computer-readable medium having stored, computer-executable instructions which, when executed by a controller 130, cause a computer to perform functions for intraoperatively providing anatomical guidance in a surgical procedure. The controller may include one or more programmable processors. In one embodiment, the functions include causing a first light source 100 in communication with the controller 130 to emit a beam of visible light to an area of interest 134 of a living subject, causing a second light source 102a that is optically coupled to an optical fiber 106 and in communication with the controller 130 to emit a beam of near-infrared light to the area of interest 134 through the optical fiber 106, and causing the optical fiber 106 of the handheld probe 104 to collect light scattered 140a from a Raman probe and/or light emitted 140b from a fluorescence probe, in response to illumination by the second light source 102a. The Raman probe 132a and/or fluorescence probe 132b is introduced into the target tissues in the area of interest 134. The functions also include causing a first imaging device 102b that is in communication with the controller 130 and the optical fiber 106 to detect the collected light 140a/140b, and causing the first imaging device 102b to generate a signal from the collected light 140a/140b that includes Raman data and/or fluorescence data. Further, the functions include causing a second imaging device 126 that is in communication with the controller 130 to detect visible light 138 that is emitted from the area of interest 134 in response to illumination by the first light source 100, causing the second imaging device 126 to generate a corresponding signal comprising visible light data, causing a third imaging device 122a that is in communication with the controller 130 to detect near-infrared light 142a having a first predetermined wavelength that is emitted from the area of interest 134 in response to illumination by the second light source 102a, and causing the third imaging device 122a to generate a corresponding signal that includes a first set of near-infrared light data.

In addition, the functions include causing a fourth imaging device 122b that is in communication with the controller 130 to detect near-infrared light 142b having a second predetermined wavelength that is different from the first predetermined wavelength and that is emitted from the area of interest 134 in response to illumination by the second light source 102a, and causing the fourth imaging device 122b to generate a corresponding signal that includes a second set of near-infrared light data. Also, the functions include generating at least one real-time integrated visual representation 146 of the area of interest 134 from the visible light data, first set of near-infrared data, second set of near-infrared data, and from the Raman data and/or fluorescence data, and causing a display 144 in communication with the controller 130 to display 144 the generated real-time integrated visual representation 146 for guidance during a surgical procedure.

In one embodiment, the function of generating the real-time integrated visual representation 146 of the area of interest 134 includes the steps of generating a wide-field image 146d of the area of interest 134 from the visible light data, generating a laser excitation image 146a of a selected area of the area of interest 134 that is defined within the wide-field image 146d from the first set near-infrared light data and/or the second set of near-infrared light data, and generating a Raman image 146b from the Raman data and/or a fluorescence image 146e from the fluorescence data, that is defined within the wide-field image 146d and the laser excitation image 146a.

In one embodiment, the Raman image 146b and/or fluorescence image 146c is an overlay image on the laser excitation image 146a. The first imaging device 102b includes a spectrometer, and each of the second imaging device 126, third imaging device 122a, and fourth imaging device 122b includes a CCD camera.

Figure 2:
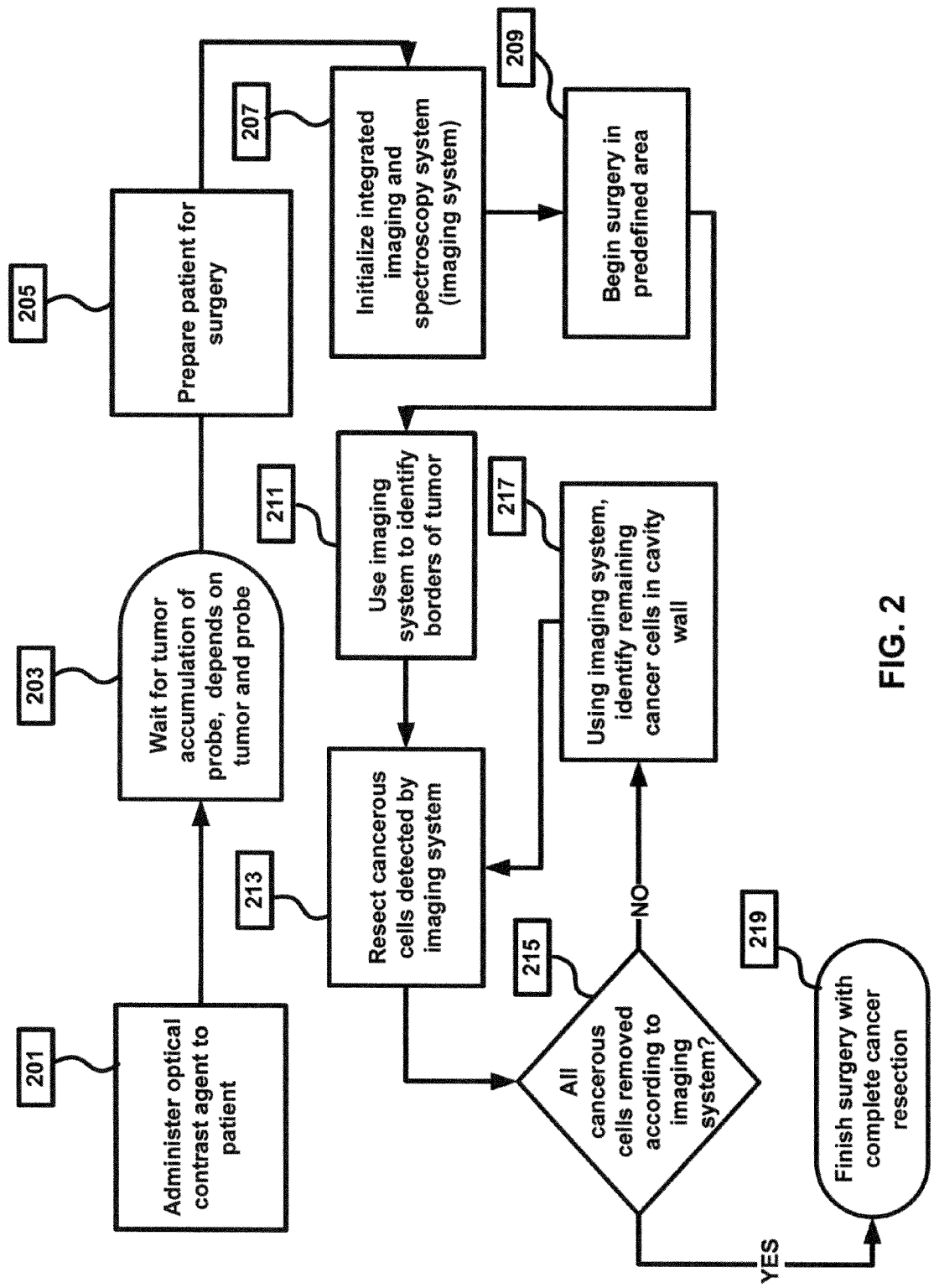
FIG. 2 is a flow chart illustrating operational steps of a method for intraoperatively providing anatomical guidance in a diagnostic or therapeutic procedure, using the system according to the embodiment shown in FIGS. 1A and 1B, according to one embodiment of the present invention.

Now referring also to FIG. 2, in yet another aspect, the present invention relates to a method for intraoperatively identifying disease in target tissues in an area of interest 134 of a living subject, to be resected in a surgical procedure. In one embodiment, the method includes the steps 201 and 203 of introducing a Raman probe and/or a fluorescence probe into the area of interest 134 until the probe has accumulated in the target tissues, the step 205 of preparing the living subject and the area of interest 134 for a surgical procedure, and the step 207 of initializing an imaging system for integrated bright-field imaging, near-infrared imaging, and Raman imaging and/or fluorescence imaging. The method also includes the step 209 of beginning the surgical procedure in the area of interest 134, the step 211 of using a first real-time integrated visual representation of the area of interest 134 and the target tissues, generated by the imaging system, to identify a boundary of the target tissues that are diseased, and the step 213 of performing a surgical resection of the identified diseased target tissues within the boundary. Further, the method includes the step 215 of, after the surgical resection, using a second displayed real-time integrated visual representation of the area of interest 134 and the target tissues, generated by the imaging system, to identify any remaining diseased target tissues within the boundary and, the step 219 of, if any remaining diseased target tissues are identified, performing a series of further surgical resections on identified remaining diseased target tissues corresponding to a respective series of real-time integrated visual representations generated by the imaging system, until the area of interest 134 is free from diseased target tissues.

In one embodiment, the imaging system includes a first light source 100 that is configured to emit a beam of visible light to an area of interest 134 of a living subject and a second light source 102a that is configured to emit a beam of near-infrared light to the area of interest 134. The system also includes a handheld probe 104 that is optically coupled to the second light source 102a, and that includes an optical fiber 106 that is configured to deliver the emitted beam of near-infrared light to illuminate the area of interest 134. The optical fiber 106 is also configured to collect light 140a that is scattered or light 140b that is emitted from a contrast agent 132a/132b introduced into target tissues in the area of interest 134, in response to illumination by the second light source 102a. A first imaging device 102b is also included in the system. The first imaging device 102b is optically coupled to the handheld probe 104 and is configured to detect the collected light 140a/140b and to generate a corresponding signal that includes collected light data. The handheld probe 104 is further configured to transmit the collected light 140a/140b to the first imaging device 102b through the optical fiber 106. The system further includes a second imaging device 126 that is configured to detect visible light 138 that is emitted from the area of interest 134 in response to illumination by the first light source 100, and to generate a corresponding signal including visible light data. A third imaging device 122a is also included in the system, which is configured to detect near-infrared light 142a having a first predetermined wavelength that is emitted from the area of interest 134 in response to illumination by the second light source 102a, and which is also configured to generate a corresponding signal including a first set of near-infrared light data. In addition, the system includes a fourth imaging device 122b that is configured to detect near-infrared light 142b having a second predetermined wavelength that is different from the first predetermined wavelength and that is emitted from the area of interest 134, in response to illumination by the second light source 102a. The fourth imaging device 122b is also configured to generate a corresponding signal that includes a second set of near-infrared light data.

A display 144 for displaying at least one visual representation 146 of data is further included in the system. Also, the system includes a controller 130 that is in communication with each of the first light source 100, second light source 102a, first imaging device 102b, second imaging device 126, third imaging device 122a, fourth imaging device 122b, and display 144. The controller may include one or more processors operative to cause a computer to perform specific functions. The controller 130 is programmed to generate at least one real-time integrated visual representation 146 of the area of interest 134 from each of the collected light data, visible light data, first set of near-infrared light data, and second set of near-infrared light data, and to display the real-time visual representation 146 on the display 144 for guidance during the surgical procedure.

In one embodiment, each of the steps of identifying diseased target tissues from the displayed real-time integrated visual representation 146 includes identifying visual representations 146a of the emitted laser excitation light 142a/142b and visual representations 146b/146c of the collected light data displayed in a selected area of the integrated visual representation 146.

IMPLEMENTATIONS AND EXAMPLES OF THE INVENTION

Without intent to limit the scope of the invention, exemplary systems and methods and their related results according to the embodiments of the present invention are given below. Note that titles or subtitles may be used in the examples for convenience of a reader, which in no way should limit the scope of the invention. Moreover, certain theories are proposed and disclosed herein; however, in no way they, whether they are right or wrong, should limit the scope of the invention so long as the invention is practiced according to the invention without regard for any particular theory or scheme of action.

Example 1

This Example relates to a handheld spectroscopic pen device utilizing exogenous contrast agents for in vivo and intra-operative cancer detection. The handheld spectroscopic pen device and near-infrared contrast agents are used for intra-operative detection of malignant tumors, based on wavelength-resolved measurements of fluorescence and surface-enhanced Raman scattering (SERS) signals. The handheld spectroscopic pen device utilizes a near-infrared diode laser (emitting at 785 nm) coupled to a compact head unit for light excitation and collection. This pen-shaped device removes silica Raman peaks from the fiber optics and attenuates the reflected excitation light, allowing for sensitive analysis of both fluorescence and Raman signals. Its overall performance has been evaluated by using a fluorescent contrast agent (indocyanine green, or ICG) as well as an SERS contrast agent (pegylated colloidal gold). Under in vitro conditions, the detection limits are approximately $2-5\times10^{-11}$ M for the indocyanine dye and $0.5-1\times10^{-13}$ M for the SERS contrast agent. Ex vivo tissue penetration data show attenuated but resolvable fluorescence and Raman signals when the contrast agents are buried 5-10 mm deep in fresh animal tissues. In vivo studies using mice bearing bioluminescent 4T1 breast tumors further demonstrate that the tumor borders can be precisely detected preoperatively and intraoperatively, and that the contrast signals are strongly correlated with tumor bioluminescence. After surgery, the handheld spectroscopic pen device permits further evaluation of both positive and negative tumor margins around the surgical cavity, raising new potential for real-time tumor detection and image-guided surgery.

Previous work [31-33] with fiberoptic devices for fluorescence and Raman measurements has not examined their suitability for measuring exogenous contrast agents during surgical procedures. In the present disclosure according to this Example, an integrated fiberoptic spectroscopic system is stably aligned and calibrated and is thus well suited for robust surgical use. One aspect of this design is that a rigid pen-sized fiber-optic unit can be used by a surgeon as a handheld device to detect small tumors and other lesions in real time during surgery. To address the issue of tumor heterogeneity, it is demonstrated that this spectroscopic system can be combined with injected contrast agents for intraoperative cancer detection and tumor margin delineation. As a result, much higher detection sensitivity and more consistent tumor signals are achieved than in previous studies that relied on native fluorescence or normal Raman scattering.

Reagents

Ultrapure water (18.2 MΩ) was used throughout the studies according to this Example. Indocyanine green (ICG), 3,3'-diethylthiatricarbocyanine iodide (DTTC), 2,2,2 tribromoethanol, tertiary amyl alcohol, and bovine serum albumin (BSA, 98%) were purchased from Sigma-Aldrich (St. Louis, Mo.). Citrate-stabilized gold colloids (60 nm diameter) at a concentration of $2.6\times10^{10}$ particles/mL were obtained from Ted Pella, Inc. (Redding, Calif.). Dulbecco's Modified Eagle's Medium (DMEM) (4.5 g/L glucose, 4.00 mM L-glutamine), fetal bovine serum (FBS), antibiotic/antimycotic solution, and phosphate buffered saline (PBS) were purchased from Thermo Scientific HyClone (Logan, Utah). XenoLight RediJect D-luciferin subtrate was purchased from Caliper Life Sciences (Hopkinton, Mass.). All reagents were used as purchased without further purification.

Handheld Spectroscopic Pen Device

A RamanProbe sampling head and connecting fiberoptics were purchased from InPhotonics (Norwood, Mass.). The cylindrical stainless steel sampling head (diameter 1.3 mm, length 10 cm) was integrated with a 5 m two-fiber cable, one for laser excitation and the other for light collection. The sampling head and fiber cable were coupled via an FC connector to a spectrometer designed by Delta Nu (Laramie, Wyo.). The combined sampling head and spectrometer system has a wavelength range of 800-930 nm with 0.6 nm spectral resolution for fluorescence measurement, and a Raman shift range of 200-2000 $cm^{-1}$ with 8 $cm^{-1}$ resolution for Raman measurement. Laser excitation was provided by a continuous-wave 200 mW diode laser emitting at 785 nm.

The handheld spectroscopic pen device was compared to a standard Raman spectrometer (Inspector, 785 nm excitation, 120 mW laser power, 0.6 nm resolution) (DeltaNu, Laramie, Wyo.) to check for wavenumber accuracy across the entire spectral range. A Raman scattering spectra from polystyrene was acquired over 5 s from both the handheld spectroscopic pen device and the commercial Raman spectrometer to determine the spectral accuracy of the handheld device. The sensitivity of the handheld spectroscopic pen device to detect ICG and SERS contrast agents was also determined. ICG was diluted in BSA solution to concentrations ranging from 25 nM to 50 pM. SERS nanoparticles were diluted in Milli-Q water to a concentration of 0.2-37.6 pM. Nanoparticle solutions of different concentrations were transferred (200 μL) into 96 well half-volume black microplates. The handheld spectroscopic pen device was fixed 10 mm above and centered over each well of the microplate. Signal collection times for each concentration ranged from 0.1 to 10 s. The relationship between the integrated signal intensity and the contrast agent concentration was statically analyzed with a linear regression model including calculated 95% confidence intervals. The statistical analyses were performed using Origin 6.1 software.

Nanoparticle Contrast Agents

Stock ICG solution was first dissolved in DMSO, and then diluted in aqueous solution containing the albumin protein (40 mg/mL, similar to the blood protein concentration). Under this condition, the ICG molecules quickly bound to albumin molecules, resulting in ICG-albumin complexes with a hydrodynamic size of 4-6 nm (diameter). The use of albumin also prevented ICG aggregation and fluorescence quenching [34]. Spectrally encoded and PEG-stabilized SERS nanoparticles were prepared according to Qian, Nie, and co-workers [26]. Briefly, aqueous diethylthiatricarbocyanine (DTTC) solution (4 μM) was added dropwise to a gold nanoparticle solution. The optimal SERS signals were detected when approximately $2 \times 10^4$ DTTC molecules were bound to each 60 nm gold particle. The particles were stabilized by the addition of a thiol-PEG solution (10 μM) and then purified by centrifugation.

Tissue Penetration Depth Measurement

Porcine tissues used for ex vivo studies were obtained from the Animal and Dairy Science Department at the University of Georgia (Athens, Ga.). Fluorescence and Raman spectra of porcine fat, liver, and lung were collected over 5-10 s. These tissues were chosen for both their relevance to disease processes and for their optical properties. To determine the depth at which the handheld spectroscopic pen device can detect fluorescent dyes or SERS nanoparticles in various organs, an 8 mm$^3$ section of the tissue was loaded with 20 μL, of either 650 nM ICG or 300 μM SERS nanoparticle solution. Next, thinly sliced sections of the corresponding tissues were laid on top of the contrast agent-loaded specimen. After each tissue section was applied, fluorescent or Raman spectra were collected over 0.1-10 s with the handheld spectroscopic pen device. A distance of 1 cm was maintained between the handheld spectroscopic pen device tip and the top tissue layer, in order to simulate the handheld spectroscopic pen device position during surgical use. A layer of plastic wrap was placed in between the contrast agent loaded tissue and subsequent tissue layers to prevent diffusion of contrast agents into the unlabeled tissue slices. Spectra were scaled as necessary to correct for different integration times and then integrated to obtain the reported signal intensity.

In Vivo and Intra-Operative Measurements

All in vivo murine studies were performed under an approved protocol by the Emory University IACUC. The mouse mammary carcinoma cell line 4T1, which stably expresses a firefly luciferase gene, was obtained from Dr. Lily Yang at Emory University (Atlanta, Ga.). 4T1 cells were cultured in DMEM containing 10% FBS and IX antibiotic/antimycotic agent. Prior to injection into mice, the cells were washed two times with PBS and diluted in sterile PBS to a final concentration of $2 \times 10^7$ cells/mL. Mammary tumors were inoculated into nude mice by the subcutaneous administration of $2 \times 10^6$ 4T1 cells into the mouse flank. Once the tumors were approximately 4 mm in diameter, ICG was administered intravenously (i.v.) via a tail vein at a dose of 357 μg/kg. After 24 h, mice were anesthetized by intraperitoneal (i.p.) injection of a 2.5% solution of tribromoethanol (350 mg/kg). Tumor-bearing mice undergoing bioluminescence imaging were administered i.p. 100 uL of a luciferin solution (30 mg/mL). Bioluminescent images were acquired on a Kodak In-Vivo FX Imaging System from Carestream Molecular Imaging (Rochester, N.Y.). Corresponding bright-field images were taken for anatomical reference of the bioluminescence signal. A series of spectra were acquired on tumor-bearing mice using the handheld spectroscopic pen device. First, the position of the handheld spectroscopic pen device was fixed to about 1-2 cm above the location of the acquisition area on the mouse. Spectra were collected in 1 s and were obtained from several locations, including directly over the center of the tumor and the peritumoral region. After the spectra were acquired, the integrated signal intensity was calculated. The signal intensity was compared to both the bright-field anatomical location and the bioluminescence signal.

Handheld Spectroscopic Pen Device Design and Performance.

Figure 3:
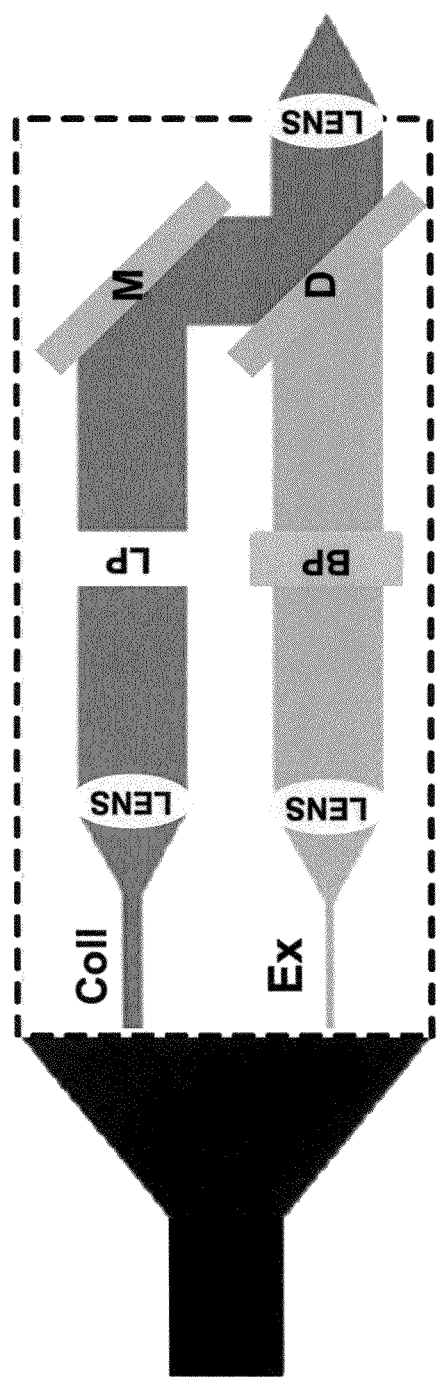
FIG. 3 schematically shows optical beam paths of a handheld spectroscopic pen device in operation, according to one embodiment of the present invention.
Figure 4:
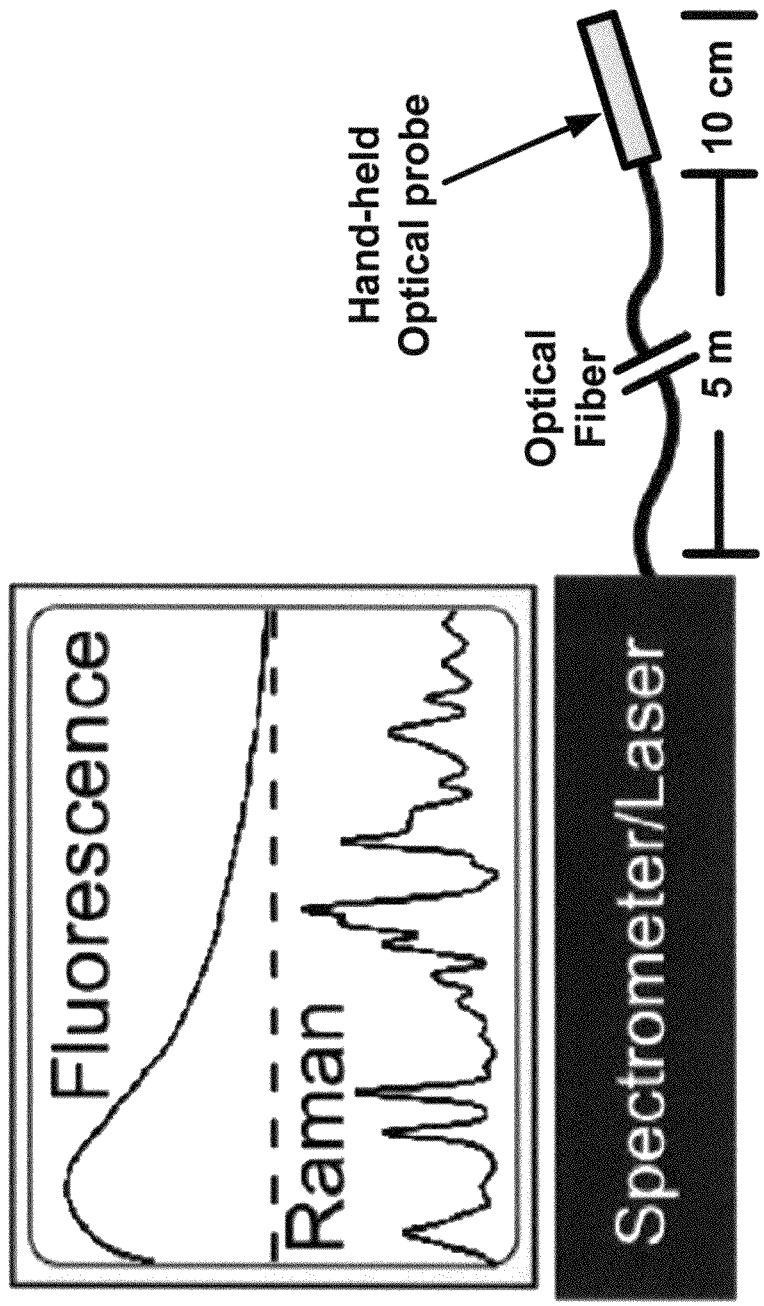
FIG. 4 schematically shows a system for wavelength-resolved fluorescence and Raman measurements, according to one embodiment of the present invention.
Figure 5:
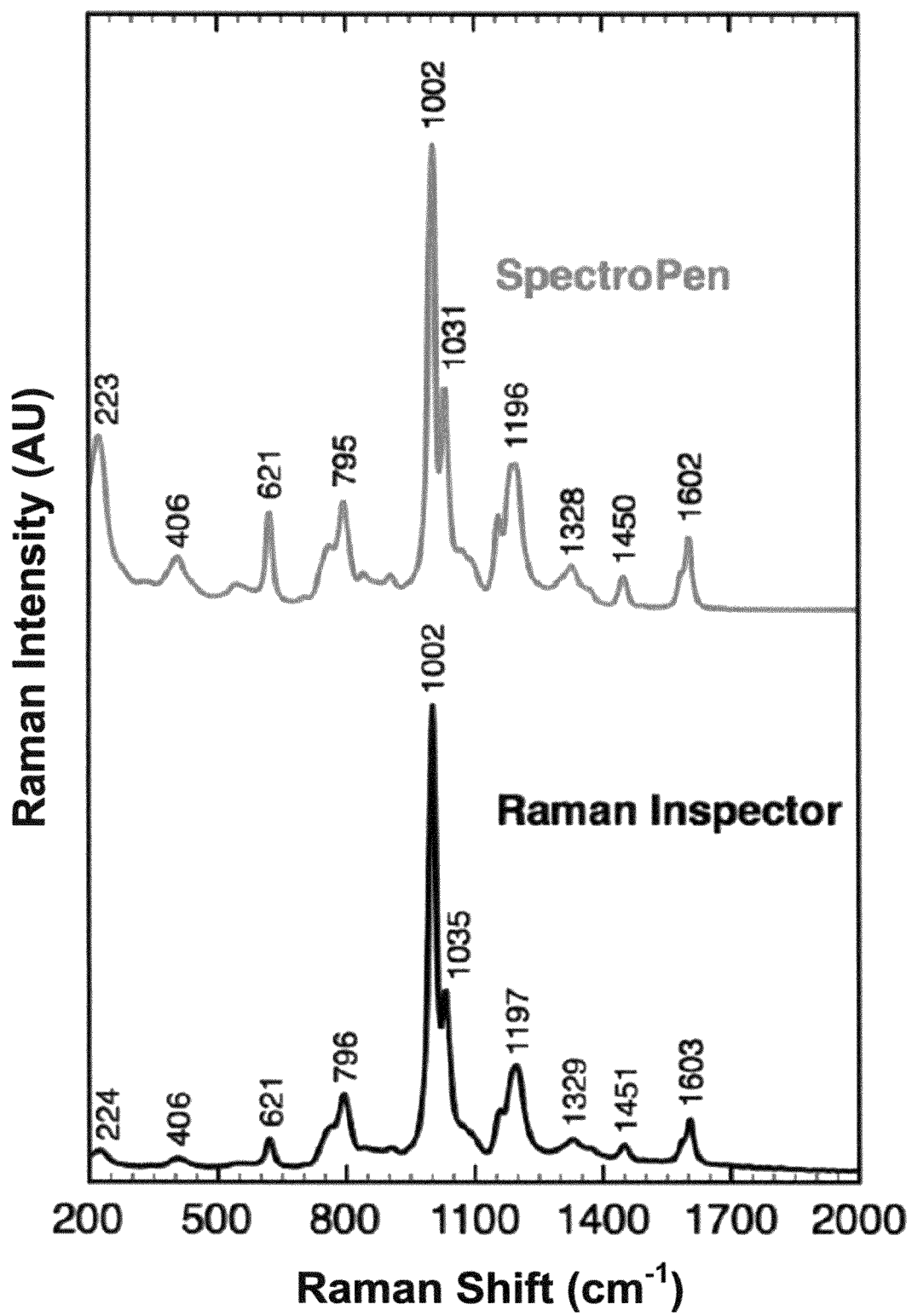
FIG. 5 illustrates Raman spectra obtained for a standard sample (polystyrene), according to one embodiment of the present invention.

The handheld spectroscopic pen device connects a handheld sampling head, via a fiberoptic cable, to a spectrometer that can record fluorescence and Raman signals. The ability to resolve NIR fluorescent and Raman signals from background tissue arises from the optical filtering that takes place in the handheld portion of the device, as illustrated in FIGS. 3 and 4. FIG. 3 schematically shows optical beam paths of a handheld spectroscopic pen device, with excitation light provided from a 785 nm laser diode (200 mW output), and having an excitation fiber ("Ex"), collection fiber ("Coll."), band-pass filter ("BP"), long pass filter ("LP"), dichroic filter ("D"), and reflective mirror ("M"). As shown, the laser light is transmitted through the excitation fiber into the pen. A first lens collimates the excitation light. Wavelength selectivity is provided by a band-pass filter. Excitation light is then focused onto the sample of interest. Backscattered light is collected through the same lens. A dichroic mirror and a long pass filter attenuate Rayleigh scattering by a factor of $10^8$ in the collection fiber. Thus, only Stokes-shifted light is transmitted to the spectrometer. Silica Raman bands arising from the optical fibers are attenuated by physical filtering in both the excitation and emission optical paths. The device's overall performance was evaluated by comparing the polystyrene Raman spectra obtained with the handheld spectroscopic pen device and a standard Raman spectrometer (see FIG. 5). The results show well matched Raman signals between the two spectrometers and also with the literature spectra of polystyrene [35]. The differences in peak positions (wavenumbers) are less than 0.5% across the entire range of 200-2000 cm$^{-1}$.

Detection Sensitivity and Dynamic Range

Figure 6A:
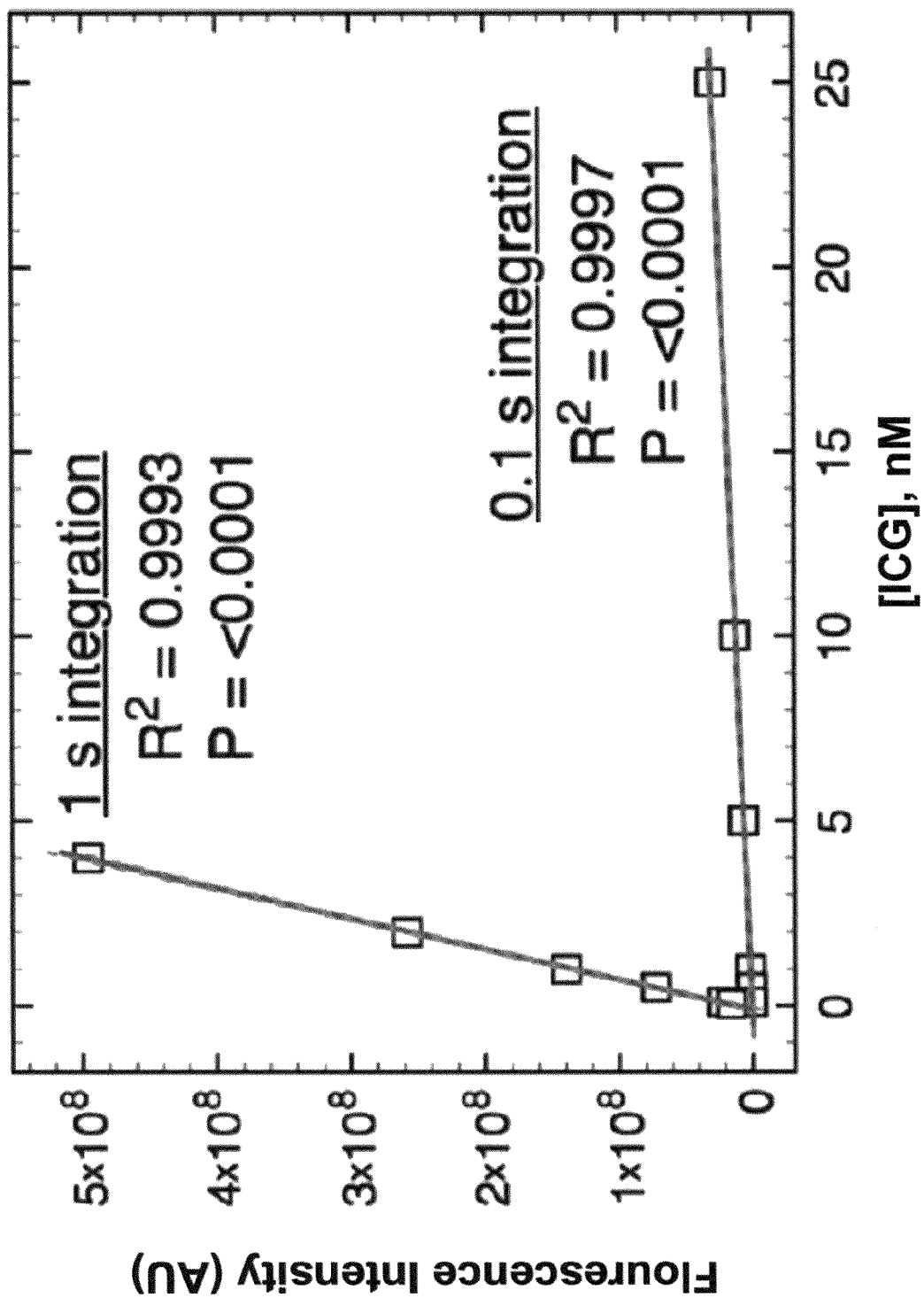
FIG. 6A illustrates fluorescence spectra obtained for various concentrations of contrast agents, according to one embodiment of the present invention.
Figure 6B:
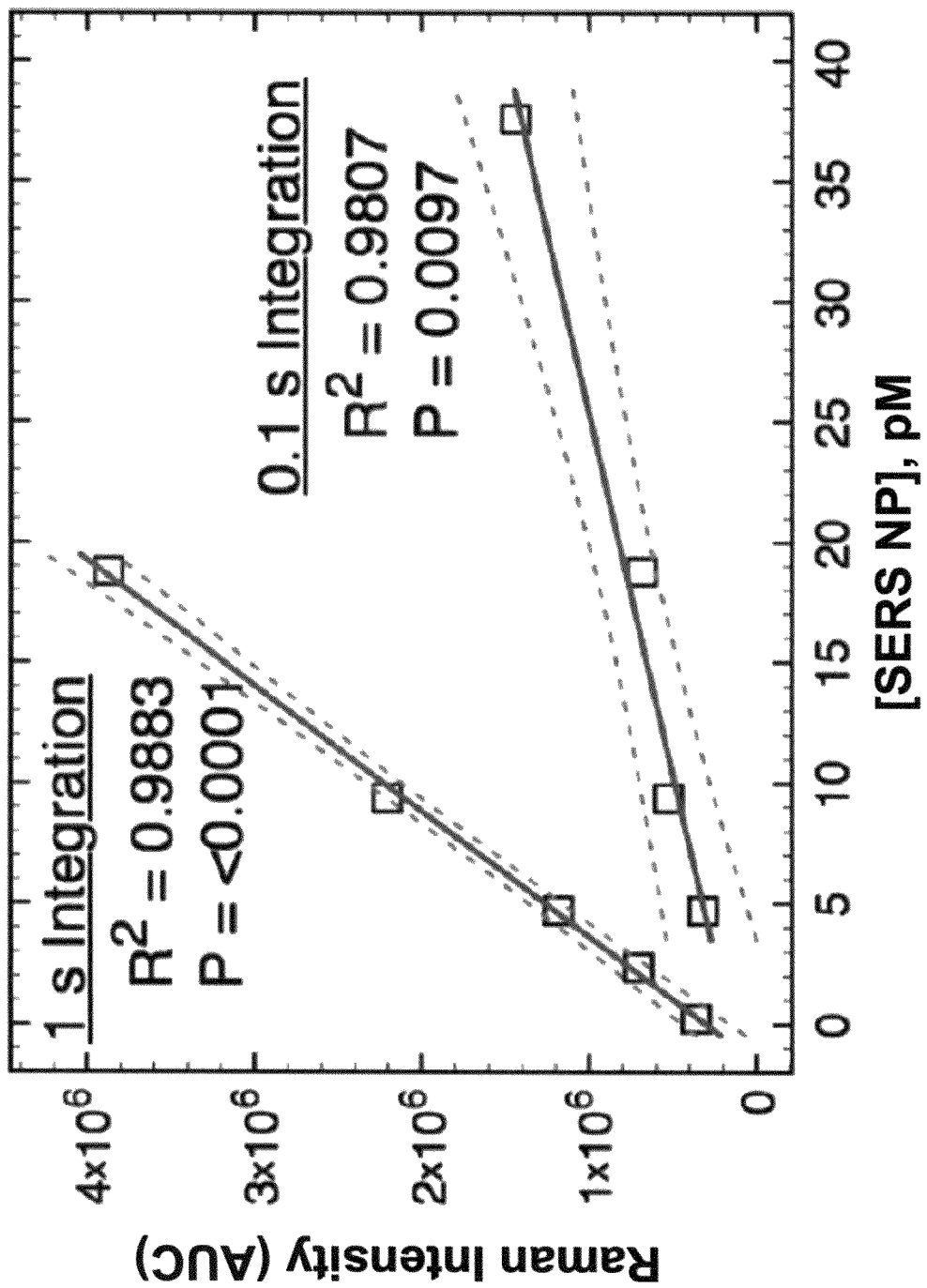
FIG. 6B illustrates Raman spectra obtained for various concentrations of contrast agents, according to one embodiment of the present invention.

As depicted in FIG. 4, the handheld spectroscopic pen device allows for sensitive detection of both fluorescent and SERS contrast agents. A linear relationship is found between the recorded signal intensity and contrast agent concentration. FIGS. 6A and 6B show the linear regression model fit to the integrated intensity versus concentration curves. The linear regression model is shown as a blue line with 95% confidence intervals shown as dashed red lines. R$^2$ is the fit coefficient of the linear regression model, and has a value of 1 for perfect fits. The P-values indicate that the slopes of the linear regression are significantly different than zero. Further examination shows a narrow 95% CI band (red dashed lines) indicating that the regression fit is very close to the "true" fit for both ICG and SERS contrast agents. The minimum spectrally resolvable concentrations (that is, limits of detection) are $2\text{-}5\times10^{-11}$ M for ICG and $0.5\text{-}1\times10^{-13}$ M for the SERS agent. The Raman reporter dye (diethylthiatricarbocyanine) used here is in resonance with the excitation wavelength at 785 nm, so the phenomenon should be called surface-enhanced resonance Raman scattering (SERRS). Also, the SERRS nanoparticles are 40-50 fold more sensitive than ICG under the above-mentioned experimental conditions, primarily because of the poor optical properties of ICG (less than 2% quantum yield and fluorescence quenching induced by aggregation). The maximum detectable concentration is determined by detector signal saturation, the analog-to-digital converter (16 bits, $2^{16}$=65,536), and the data integration time. That is, for low contrast signals, the integration time should be increased in order to improve the signal-to-noise ratio, whereas for high contrast signals, the integration time should be reduced to avoid detector saturation (which will allow high-speed acquisition of tumor contrast signals). The dynamic range is then defined by the low and high limits in which the contrast signal intensity is linear with its concentration. For both fluorescence and Raman measurements, the handheld spectroscopic pen device provides a 50-60 fold dynamic range. Accordingly, weak tumor-margin signals that are 50-60 fold lower than the central tumor signals can be measured simultaneously without adjusting the data acquisition parameters, as further discussed below.

Spectral Discrimination and Tissue Penetration Depth

An objective of intraoperative use of the handheld spectroscopic pen device is detection of tumor foci at the margins of the tumor mass, thereby minimizing the risk of positive margins. In practice, a real-time detection system according to aspects of the exemplary embodiment disclosed in this Example allows the surgeon to remove tumor tissue that might have gone undetected, saving the patient from repeated surgery and potentially improving survival. Sensitive tumor detection is based on the use of albumin-bound ICG or SERS nanoparticles as contrast agents. As discussed in more detail later, the main mechanism is believed to be "passive tumor targeting" in which nanoparticles are accumulated and retained in the tumor interstitial space mainly through the enhanced permeability and retention (EPR) effect [36, 37].

The ability of the handheld spectroscopic pen device to differentiate contrast agent signals from the autofluorescence and Raman scattering of major tissue/organ types (i.e. fat, liver and lung) was first examined. FIG. 4A shows representative spectra of pure ICG, animal fat, and a mixture of ICG and animal fat (ICG in fat). At 785 nm excitation, ICG has a fluorescence peak at 816 nm, while fat has a background fluorescence peak at 805 nm plus resolvable Raman signals at 862, 1070, 1297, 1439, and 1652 $cm^{-1}$ (corresponding to 842, 857, 874, 885, and 902 nm in wavelength, respectively). ICG buried in fat has identifiable contributions of both ICG and fat (e.g., ICG fluorescence at 816 nm and the fat Raman peaks at 874 and 885 nm).

Figure 7A:
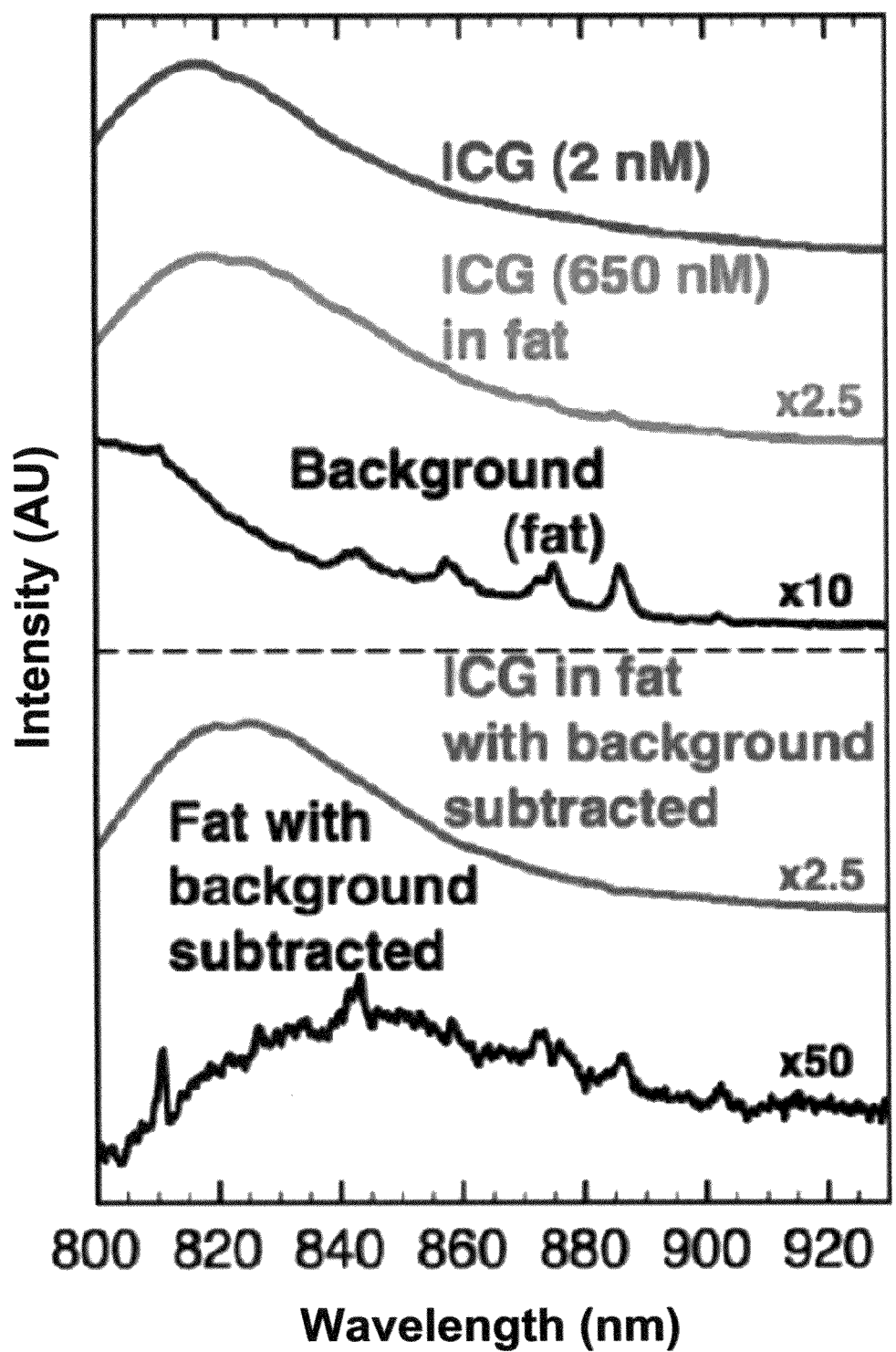
FIG. 7A illustrates fluorescence spectra obtained before background signal subtraction (upper panel) and after background signal subtraction (lower panel), according to one embodiment of the present invention.
Figure 7B:
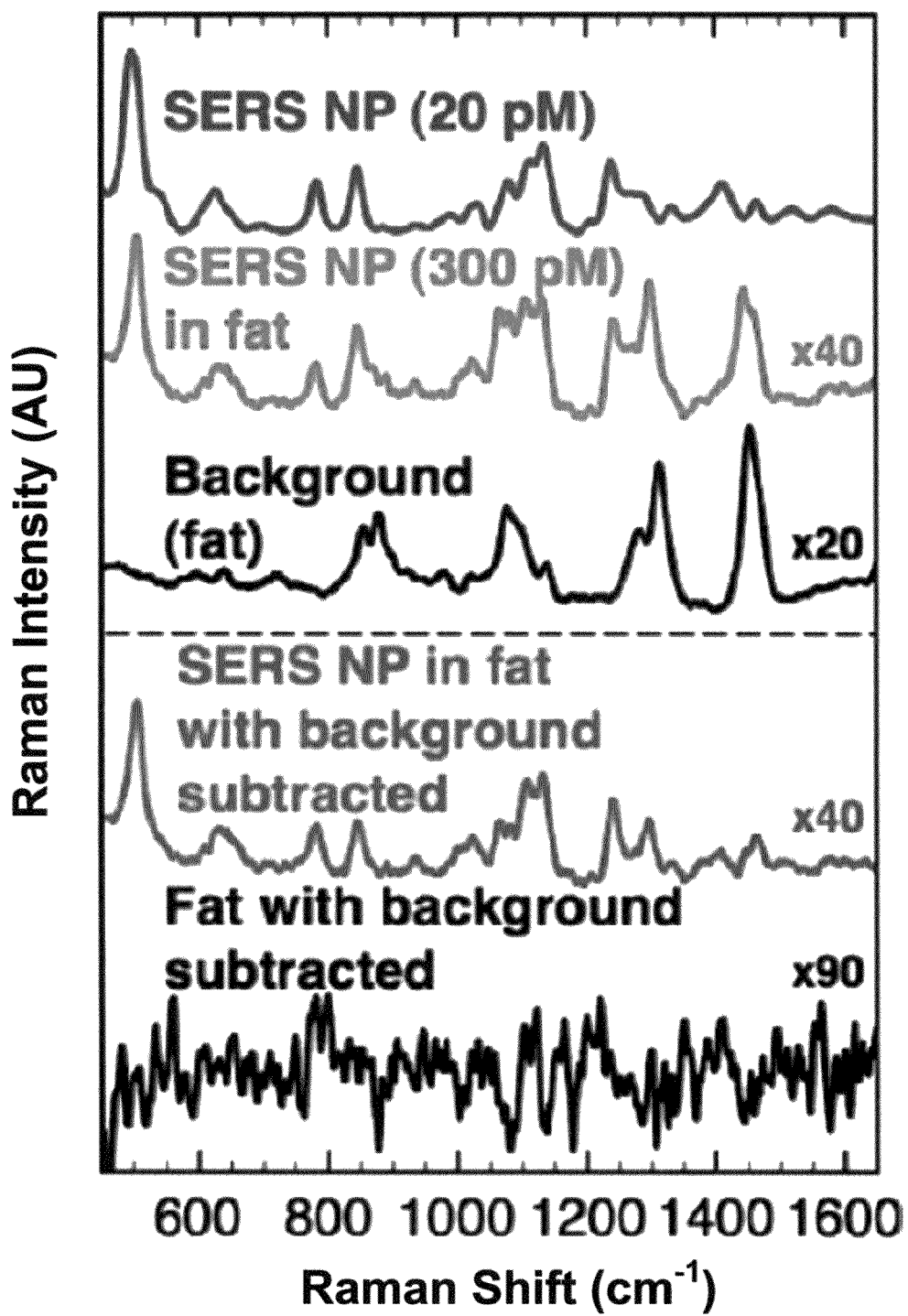
FIG. 7B illustrates Raman spectra obtained before background signal subtraction (upper panel) and after background signal subtraction (lower panel), according to one embodiment of the present invention.
Figure 8:
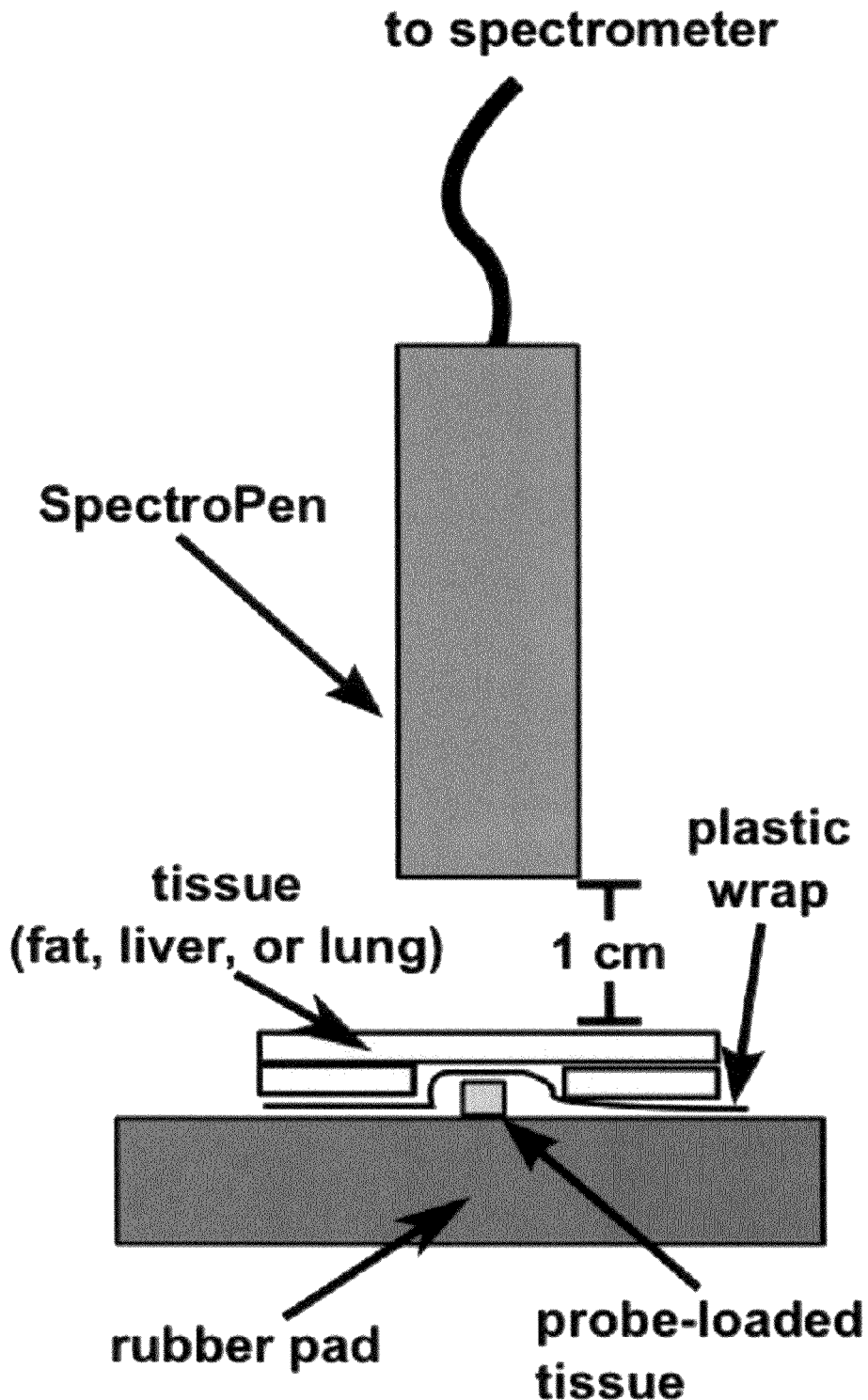
FIG. 8 schematically shows a system for performing tissue penetration depth studies of near-infrared fluorescent and SERS contrast agents, according to one embodiment of the present invention.

FIG. 7A illustrates fluorescence spectra of pure ICG, animal fat, and a mixture of ICG and animal fat before background subtraction (upper panel) and after background subtraction (lower panel). FIG. 7B illustrates Raman spectra of pure SERS nanoparticles, animal fat, and a mixture of SERS nanoparticles and animal fat before background subtraction (upper panel) and after background subtraction (lower panel). All spectra were taken with the handheld spectroscopic pen device positioned 1 cm above the top layer of tissue. Spectra were acquired over 0.1-10 s. The background was obtained by averaging four different spectra obtained from control tissues, and was subtracted from the contrast-enhanced spectra or from single background measurements. Signal intensities relative to that of pure ICG or SERS samples are indicated by scaling factors. The Raman reporter dye was diethylthiatricarbocyanine (DTTC);

As shown in FIG. 7A (lower panel), the background signal of fat can be accurately subtracted, allowing nearly pure ICG contrast signals. Similarly, the data in FIG. 7B (upper and lower panels) show that the background Raman spectrum can be subtracted to reveal predominantly the SERS contrast signals. As noted earlier, the ability to detect deeper satellite residual tumors adjacent to the primary tumor is important to complete tumor resection and improving patient outcome. To simulate this surgical scenario, the ability of the handheld spectroscopic pen device to detect optical contrast agents below the surface of fat, liver, and lung tissues was examined, by placing contrast agent loaded tissue specimens below 1-2 mm sections of unlabeled tissue (FIG. 8). FIG. 8 schematically shows a system for performing tissue penetration depth studies of near-infrared fluorescent and SERS contrast agents.

Figure 9A:
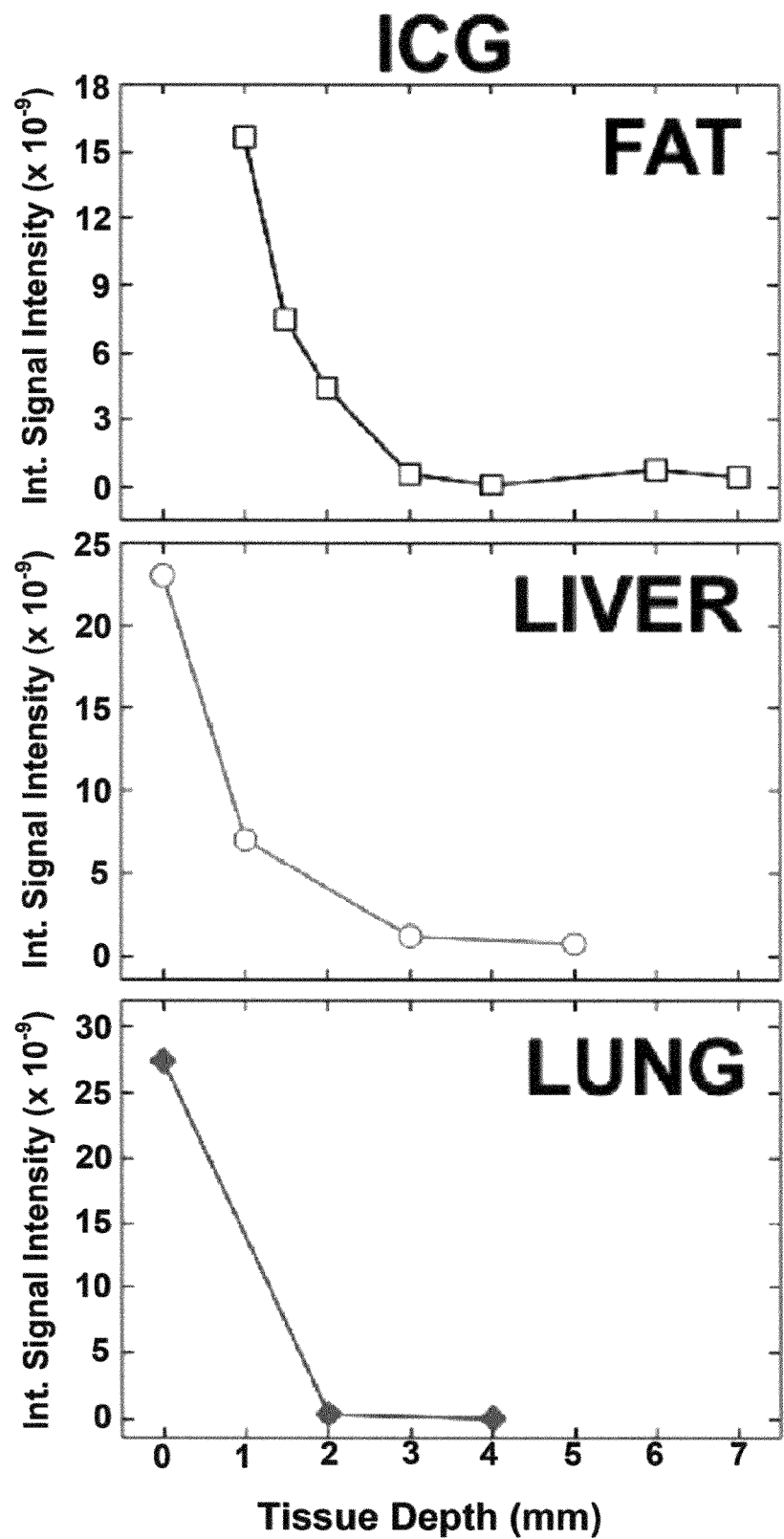
FIG. 9A illustrates ICG signals as a function of placement depth of contrast agents in fresh fat, liver, and lung tissue, according to one embodiment of the present invention.
Figure 9B:
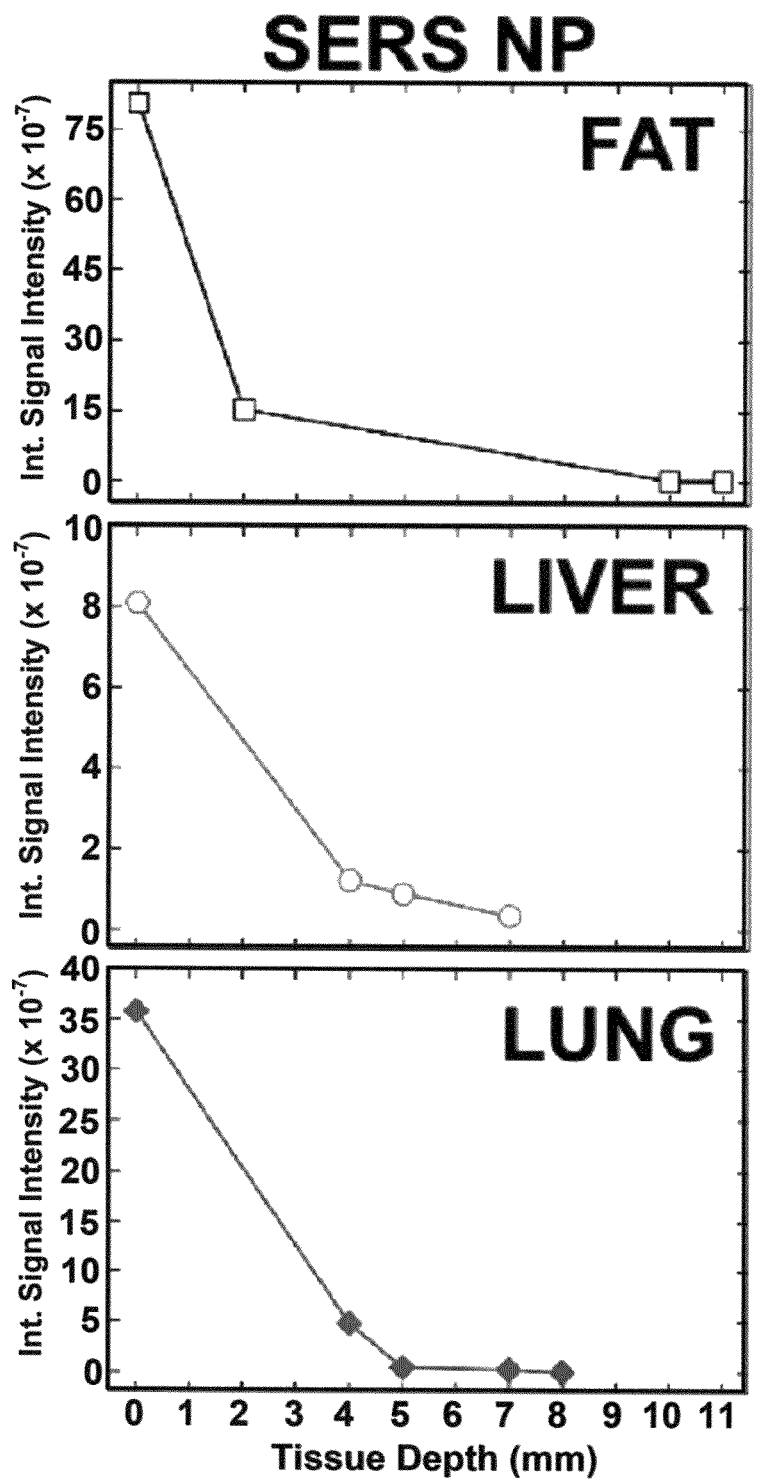
FIG. 9B illustrates SERS signals as a function of placement depth of contrast agents in fresh fat, liver, and lung tissue, according to one embodiment of the present invention.

FIGS. 9A and 9B show the relationship between signal intensity and the depth of ICG or SERS agents deeply placed in ex vivo tissues. As expected from light scattering, the contrast signal intensity decreased almost exponentially with tissue thickness. ICG can be detected more deeply in fat than other tissues because fat does not scatter the excitation light as strongly as lung and liver. This finding has potentially important applications in lipomatous (fat-rich) tissues such as breast and some other soft tissues. In addition, lung and liver have more intense autofluorescence with NIR excitation (likely due to porphyrins and related chromophores in these highly vascularized organs), which compromises the ability to distinguish ICG emission from native autofluorescence. In comparison, SERS nanoparticles give rise to sharp spectral peaks that are distinct from the broad background, allowing accurate extraction of weak SERS signals under high-attenuation and scattering conditions. Thus, weaker SERS signals can be detected and resolved at a greater tissue depth in comparison with ICG fluorescence. The penetration depth can be further improved by positioning the fiberoptic tip closer to the tissue surface (almost in contact).

In Vivo and Intra-Operative Tumor Detection

Figure 10A:
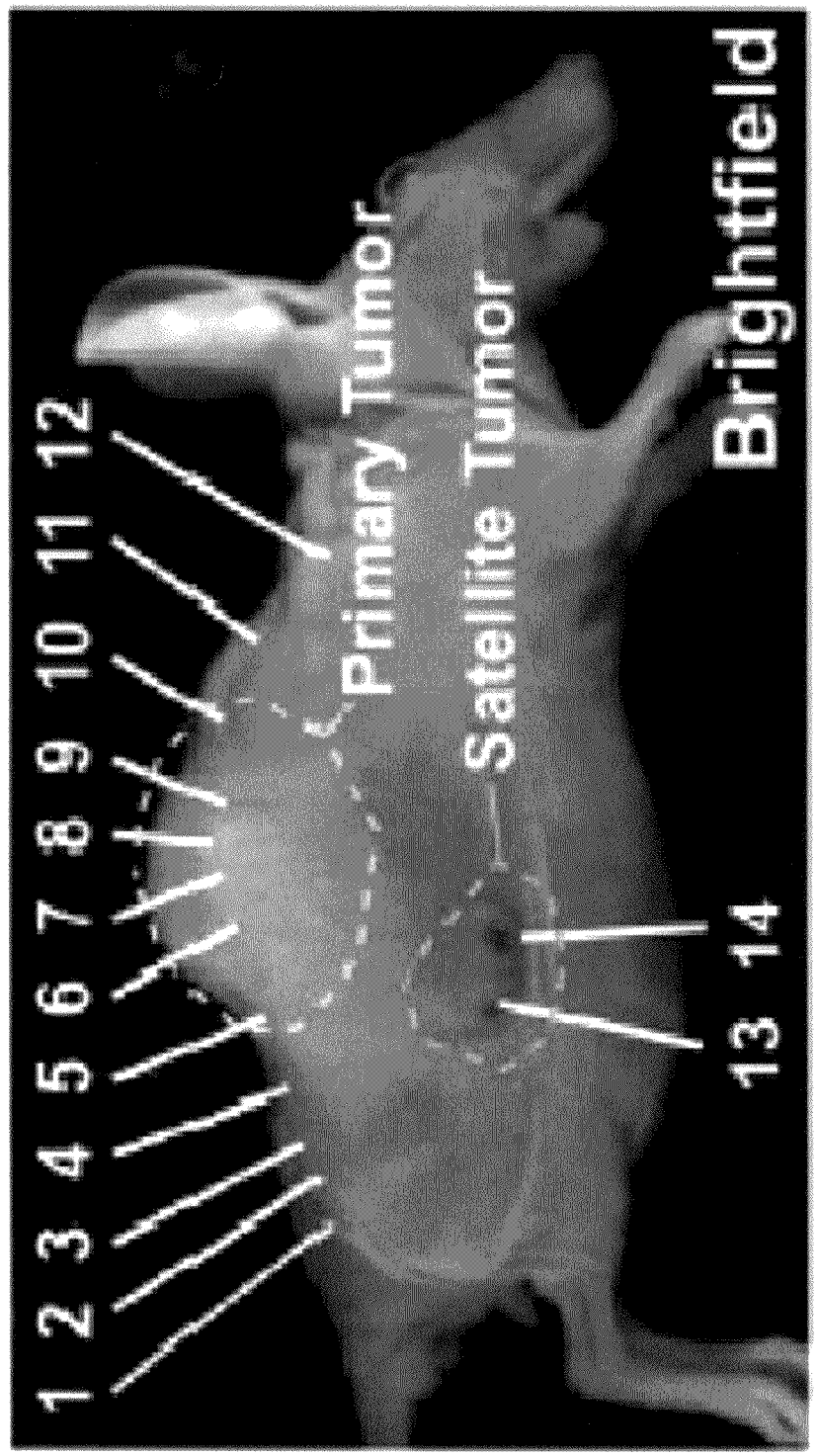
FIG. 10A shows a bright-field image identifying anatomical locations of a primary tumor and two satellite nodules (dashed circles), according to one embodiment of the present invention.
Figure 10B:
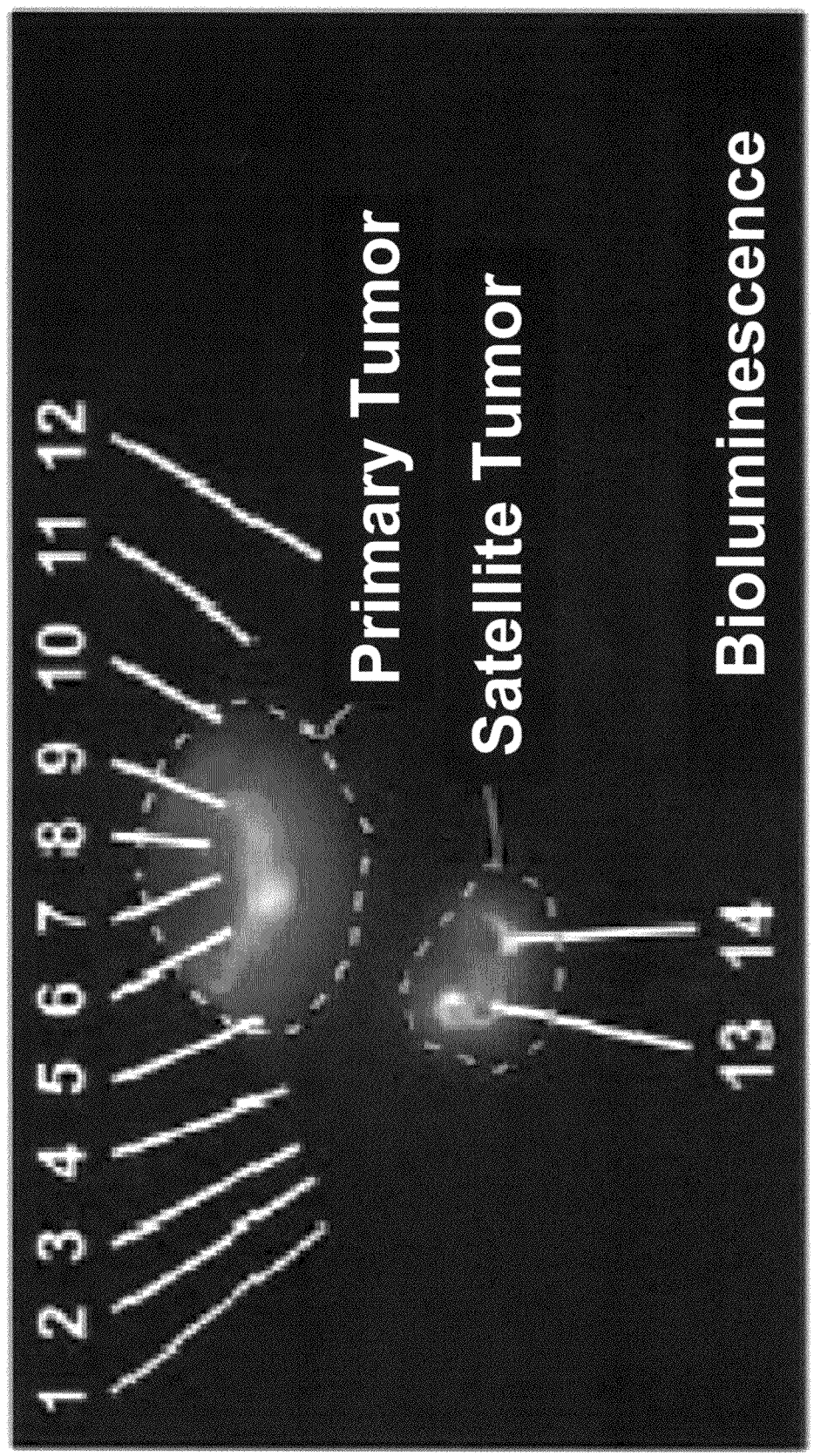
FIG. 10B shows a bioluminescence image of a mouse, identifying the primary and satellite tumors (red signals), according to one embodiment of the present invention.

In vivo investigations were conducted to test the ability of the handheld spectroscopic pen device to detect intratumoral deposition of ICG after intravenous infusion. This contrast agent has been approved by the U.S. Food and Drug Administration (FDA) and is indicated for various uses in humans, such as for determining cardiac output, hepatic function and liver blood flow, and for ophthalmic angiography [38]. To assess degree of tumor contrast enhancement using ICG, mice were used in which 4T1 tumor cells ($2\times10^6$ in number) were subcutaneously injected 18 days prior to imaging. The tumor cells were genetically engineered to express the firefly luciferase gene; intravenous injection of luciferin after tumor development causes these cells to emit bioluminescent light and allows one to determine the precise location of tumors using bioluminescence imaging. Thus, ICG contrast enhancement can be correlated with simultaneous bioluminescence imaging to determine whether ICG contrast enhancement (if any) originated from tumor sites. On day 17 after tumor cell inoculation, ICG was intravenously infused into the mice using a dose of 357 μg/kg, which is the equivalent dose used for human use, and then imaged the mice using the handheld spectroscopic pen device 24 h later. Using bioluminescence imaging, a dominant tumor site was identified, along with two satellite tumor sites along the track of the needle used for inoculation of tumor cells (FIGS. 10A and 10B). A set of 14 spectra was obtained from the mouse using the handheld spectroscopic pen device.

Specifically, FIG. 10A shows a bright-field image identifying the anatomical locations of a primary 4T1 breast tumor and two satellite nodules (dashed circles). The specific locations for measurement using a handheld spectroscopic pen device are indicated by numbers 1-12 for the primary tumor and 13-14 for the satellite nodules. FIG. 10B shows a bioluminescence image of the mouse, identifying the primary and satellite tumors (red signals).

Figure 11:
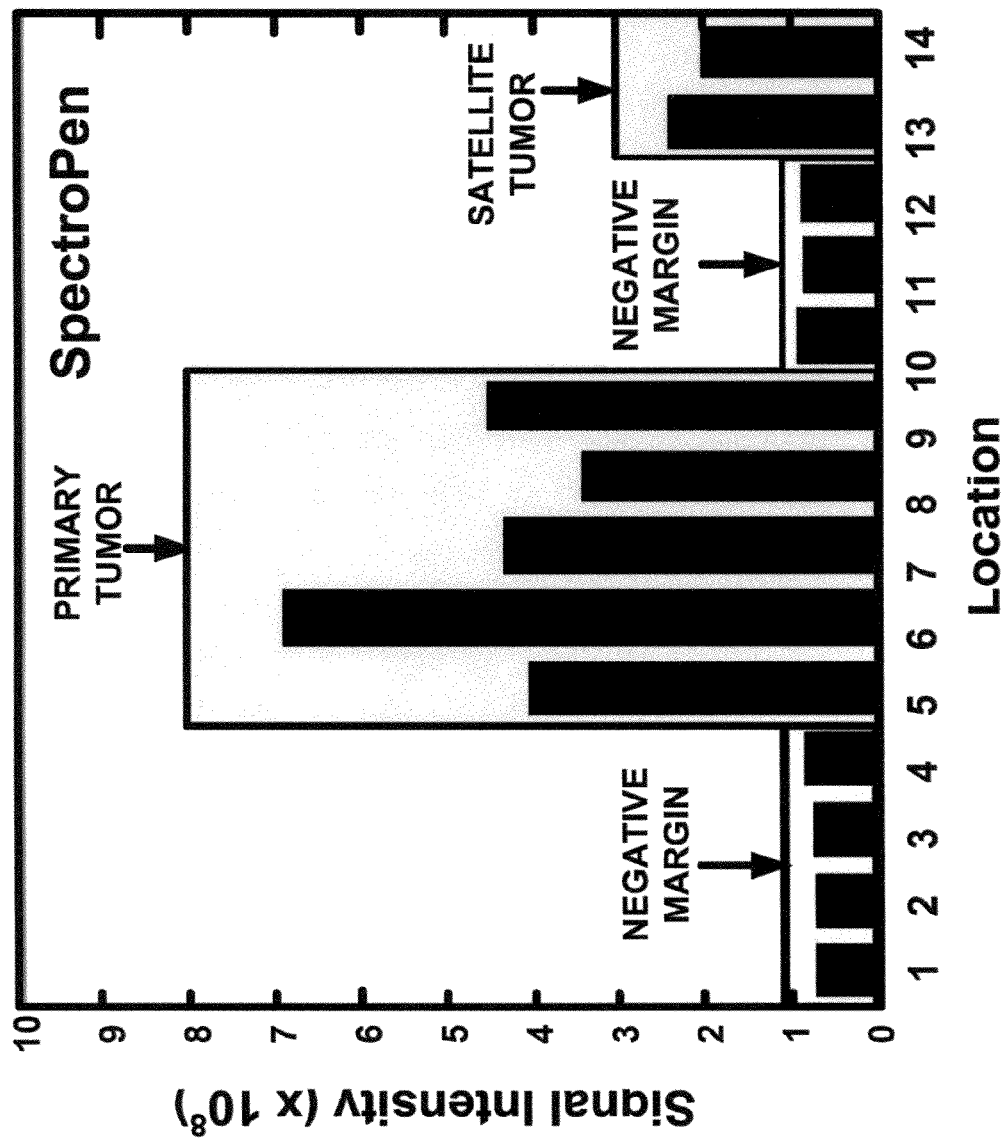
FIG. 11 illustrates ICG signal intensities detected at various locations identified in FIGS. 10A and 10B.

FIG. 11 highlights the high degree of ICG contrast enhancement in the tumors as compared to the surrounding tissues. The intense ICG signals at locations 5-9, 13, and 14 are indeed correlated with the presence of tumor as determined by bioluminescence. The integrated signal intensities from the tumor areas are nearly 10 times more intense than the signals obtained from normal regions. Spectra collected from the adjacent edges (less than 2 mm from the tumor) are still 5-6 times stronger than that of the more remote areas, providing excellent delineation of the tumor. After surgical removal of the tumors, bioluminescence imaging shows that the excised tumors are bright and the surgical cavity is dark (see FIGS. 12A and 12B).

Figure 12A:
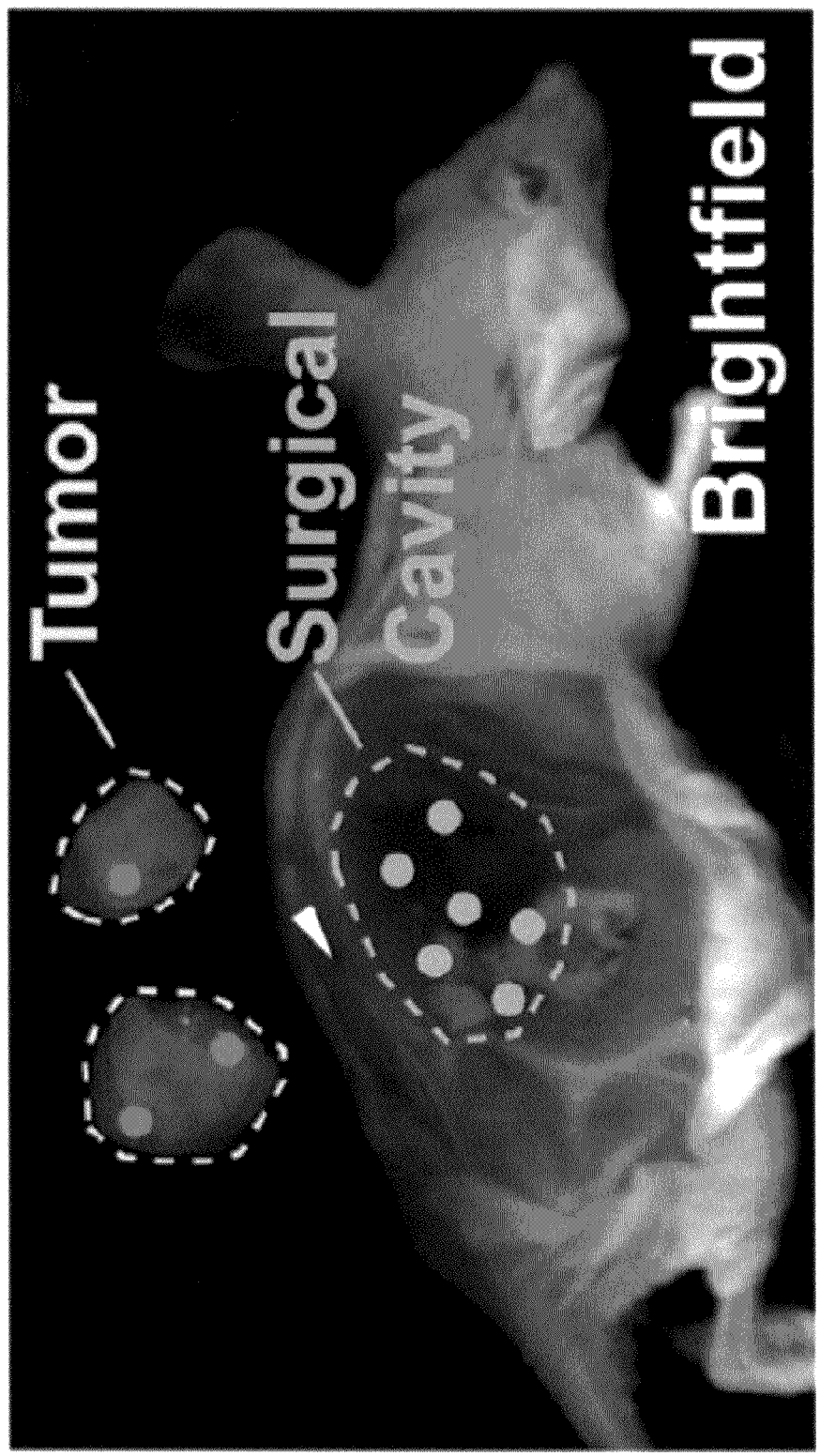
FIG. 12A shows a bright-field image identifying a resected tumor (yellow dashed lines) and surgical cavity (cyan dashed line), obtained by detection of positive and negative tumor margins, with a region having a residual tumor along the margin of the cavity, as detected by its signal intensity, according to one embodiment of the present invention.
Figure 12B:
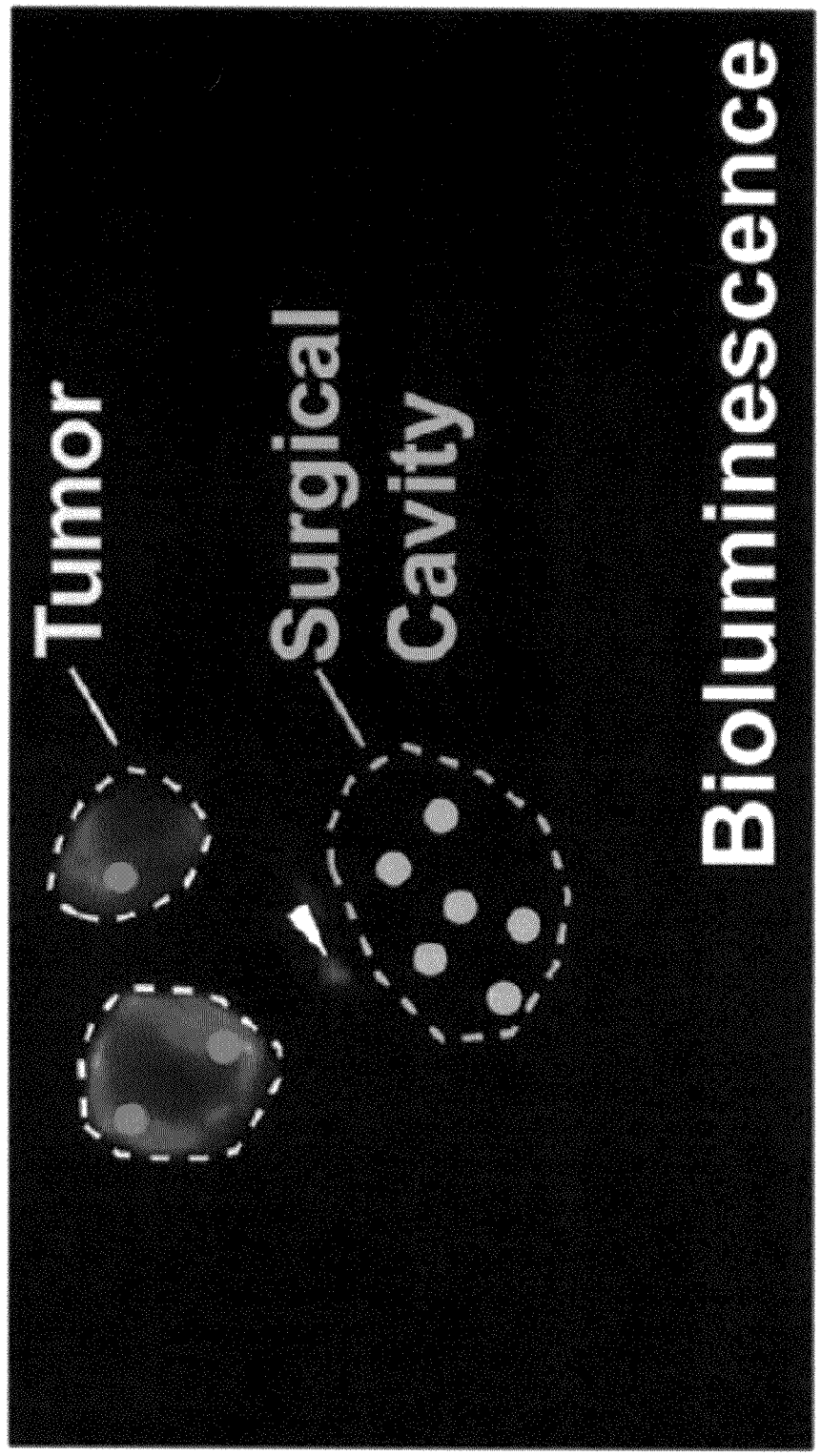
FIG. 12B shows a bioluminescent image identifying a resected tumor (yellow dashed lines) and the surgical cavity (cyan dashed line), where spectra obtained within the excised tumor are shown in red, those in the surgical cavity are shown in cyan, and one on the margin of the surgical cavity is shown by a white arrowhead, according to one embodiment of the present invention.

Specifically, FIGS. 12A and 12B show bright-field images (FIG. 12A) and bioluminescent images identifying positive and negative tumor margins detected using a handheld spectrometer pen device, including a resected tumor (yellow dashed lines) and the surgical cavity (cyan dashed line). Spectra obtained within the excised tumor are shown in red, those in the surgical cavity are shown in cyan, and one on the margin of the surgical cavity is shown by a white arrowhead. As seen on the bioluminescence image, there was a region with residual tumor along the margin of the cavity.

Figure 13:
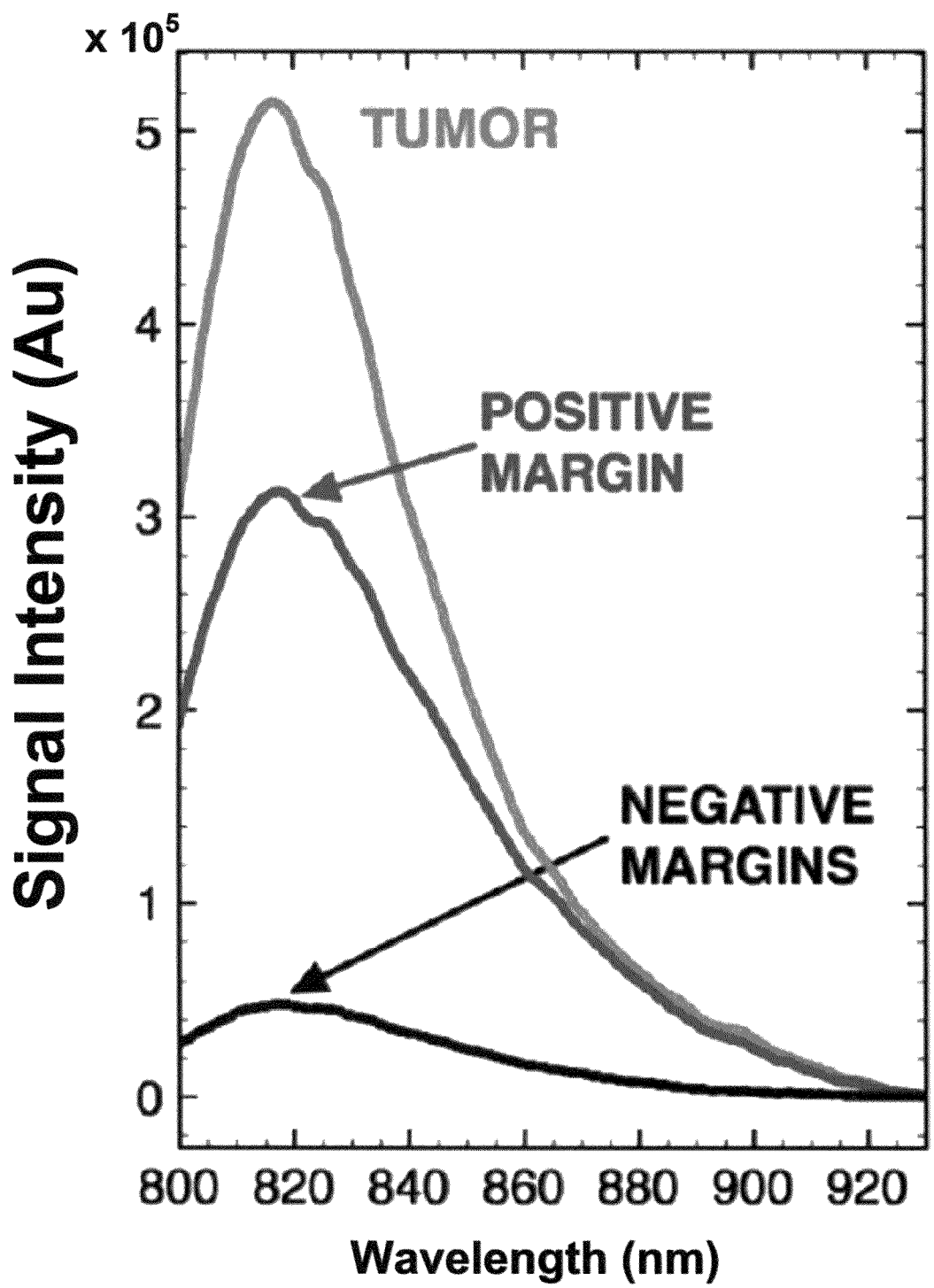
FIG. 13 illustrates averaged spectra from tumors and positive and negative margins, according to one embodiment of the present invention.

Referring to FIG. 13, spectra recorded by the handheld spectroscopic pen device indicate 10-fold stronger signals for the excised tumors as compared to the cavity, which is consistent with the contrast ratio of tumor to healthy tissue found within the living animal (see FIG. 11).

There was a very small area of bioluminescence remaining at the margin of the cavity, corresponding to a positive surgical margin, that was not seen by visual inspection alone. Reexamination of this area with the handheld spectroscopic pen device revealed an ICG signal that was 5 times stronger than for adjacent tissue, again consistent with the contrast ratios recorded from noninvasive imaging. The ability to obtain a strong ICG signal from tumor, remove the tumor as guided by the handheld spectroscopic pen device, and obtain real-time pathology about the margin status of both excised tissue and the remaining tumor cavity, are all important features for image-guided surgery.

Results indicate that the observed ICG contrast between tumor and normal tissues is very clear and strong, even though no tumor-targeting ligands are used in this work. Previous oncology studies utilizing ICG are mainly directed toward sentinel lymph node detection [39-42]. These studies rely on direct intratumoral or peritumoral injections of ICG rather than the intravenous route of administration as used in the study according to the present Example. After intravenous administration, ICG is known to bind to the hydrophobic pockets of serum proteins, especially albumin and lipoproteins [38]. Thus, through protein binding, ICG takes on nanometer scale dimensions, with a hydrodynamic size of 6-8 nm diameter. The strong tumor enhancement comes from the enhanced permeability and retention (EPR) effect [43], in which macromolecules or nanoparticles preferentially accumulate in tumor due to the abnormal neovasculature with large fenestrations and poor lymphatic drainage characteristic of tumors. More advanced nanoparticle formulations of ICG have been reported to facilitate longer circulation of ICG and increased tumor accumulation for diagnostic and photothermal applications [44-47]. Also, targeted contrast agents can be developed by conjugating SERS and other nanoparticles to peptides, monoclonal antibodies, and small-molecule ligands for molecular recognition of antigens or receptors on the surface of tumor cells [48].

In summary, according to the present Example, a handheld spectroscopic device was constructed and the use of two near-infrared contrast agents for in vivo and intraoperative tumor detection has been shown. Under in vitro conditions, the handheld device provides a detection limit of $2-5 \times 10^{-11}$ M for ICG and a detection limit of $0.5-1 \times 10^{-13}$ M for SERS. The tissue penetration depth is about 5-10 mm depending on the tissue's optical properties and the ability to resolve weak contrast signals. In addition, in vivo studies were carried out by using mouse models bearing bioluminescent 4T1 breast tumors. The results indicate that the tumor borders can be precisely detected preoperatively and intraoperatively, resulting in real-time detection of both positive and negative tumor margins around the surgical cavity. In comparing the two types of near-infrared contrast agents, SERS nanoparticles (60-80 nm) provide rich spectroscopic information (sharp spectral features), but are much larger than the ICG-albumin complexes (4-6 nm). Accordingly, the SERS agent may be better suited for mapping blood vessels and tumor boundaries/peripheries (important for delineating tumor margins), whereas ICG-albumin may be better suited for tumor penetration and rapid clearance.

Example 2

This Example relates to an integrated imaging and spectroscopy system for image-guided surgery. According to one embodiment, the system is configured to detect the signal from a fluorescent or Raman-active probe introduced into a patient and localized to a disease area of interest (e.g. a tumor). A surgeon using this system may totally remove a diseased area and verify that the diseased area was successfully and entirely removed.

According to one embodiment of the present Example, a multi-modal imaging system comprises a wide-area imaging system that is configured for imaging in the visible and near-infrared light ranges (400-1000 nm), and a narrow-beam combination fiberoptic laser light excitation source (633 nm or 785 nm) and spectroscopy detector. The wide-area imaging system has one lens and three cameras: one color camera to detect and record visible light (400-610 nm, what a user sees with the unaided eye); one black and white camera to detect the light from the laser excitation source (633 nm or 785 nm); and one black and white camera to detect the light emitted from a probe (e.g. 850 nm). Physical optical filters (bandpass for emission selectivity, laser line/notch to block laser excitation light on all but the "laser camera," and dichroic mirrors to split the desired light among the three cameras) are used to split the light collected from a single lens into the three individual cameras and to provide specificity for the desired wavelengths of light to reach each camera. The system is used alongside fluorescent (e.g. indocyanine green dye, quantum dot) or surface-enhanced Raman scattering (SERS) probes injected into the subject and accumulated by passive or active targeting to an area corresponding with diseased tissue. When in use, the information from the cameras is processed by a computer and displayed such that the user may see the visual field; an overlay onto the image of the visual field shows the position of the laser illumination and the light illumination of the probe (if present). A computer uses image processing to enhance the image of the visual field, making it easier to distinguish the position of the probe in relation to the surrounding tissue. Simultaneously, the fiber-optic laser illumination and spectroscopy detector displays a spectrum of the light emitted from the area illuminated by the laser light. The spectroscopy system is operative to detect the fluorescence emission and Raman light scattering of both native tissue and the introduced probes.

Example 3

This example relates to a method for condensing spectrograph information recorded by a "Raman pen" spectrometer onto a wide-field video display (see also the system according to Example 2, above), also referred to as "virtual phosphorescence." According to one embodiment, the virtual phosphorescence display mode is a way to overlay information recorded continuously from a Raman pen spectrometer onto a wide-field image. Data recorded from the spectrometer is a spectrum (the intensity of light at a given wavelength). For fluorescence probes, data is analyzed in a simple area-under-the-curve (AUC) method (ratio of integrated fluorescence to minimum/background); for Raman scattering probes (and optionally for fluorescence probes), a computationally more complex deconvolution method is used (match known spectra to the recorded spectra via optimization). A positive signal is assumed when the fluorescence AUC ratio is over a predetermined threshold or when the AUC ratio of the spectra obtained through deconvolution are over a predetermined threshold. In both cases, the predetermined threshold is at least 3 standard deviations above the background signal level, and corresponds to a significant amount of fluorescent or Raman probe in the sample area of the spectrometer.

When a positive signal is recorded, a false color overlay is placed on the wide-field image at the location of a laser excitation source when the signal was recorded (the location is detected by the camera dedicated for laser tracking). The overlay decays over time. That is, initially the overlay will be bright, but over the course of seconds the overlay will become progressively more translucent (and so appear dimmer). The decay time is user-selectable, so for very static conditions, such as when the surgical area is being swept by the Raman pen to locate tumor boundaries, a longer decay time (e.g. 5 seconds) is used to indicate where positive signals are recorded. For dynamic conditions, such as when a surgeon is actively cutting tissue under image guidance, the decay time is short (e.g. 1 second) to accurately indicate where positive tumors are recorded.

The foregoing description of the exemplary embodiments of the invention has been presented only for the purposes of illustration and description and is not intended to be exhaustive or to limit the invention to the precise forms disclosed. Many modifications and variations are possible in light of the above teaching.

The embodiments were chosen and described in order to explain the principles of the invention and their practical application so as to enable others skilled in the art to utilize the invention and various embodiments and with various modifications as are suited to the particular use contemplated. Alternative embodiments will become apparent to those skilled in the art to which the present invention pertains without departing from its spirit and scope. Accordingly, the scope of the present invention is defined by the appended claims rather than the foregoing description and the exemplary embodiments described therein.

LIST OF REFERENCES

[1] De Grand, A. M. et al., *Technol. Cancer. Res. Treat.* 2003, 2, 553-562.
[2] Gebitekin, C. et al., *Eur. J. Cardiothorac. Surg.* 1994, 8, 334 and 339-343.
[3] Meric, F. et al., *Cancer* 2003, 97, 926-933.
[4] Karakiewicz, P. I., et al., *Urology* 2005, 66, 1245-1250.
[5] Kuvshinoff, B. et al. *Surg. Oncol.* 2001, 8, 163-169.
[6] Sienel, W. et al. *Eur. J. Cardiothorac. Surg.* 2007, 31, 522-528.
[7] Karni, T. et al., *Am. J. Surg.* 2007, 194, 467-473.
[8] Neoptolemos, J. et al., *Ann. Surg.* 2001, 234, 758-768.
[9] Gambhir, S. S. *Nat. Rev. Cancer* 2002, 2, 683-693
[10] Townsend, D. W. *J. Nucl. Med.* 2001, 42, 533-534.
[11] Ramina, R. et al., *Acta Neurochir* 2010, 152, 27-33.
[12] Ngo, C. et al., *Ann. Surg. Oncol.* 2007, 14, 2485-2489.
[13] Dacosta, R. S. et al., *Best Pract. Res. Clin. Gastroenterol.* 2006, 20, 41-57.
[14] Draga, R. O. et al., *Anal. Chem.* 2010, 82, 5993-5999.
[15] Haka, A. S. et al., *Cancer Res.* 2006, 66, 3317-3322.
[16] Mo, J. et al., *Anal. Chem.* 2009, 81, 8908-8915.
[17] Schwarz, R. A. et al., *Cancer* 2009, 115, 1669-1679.
[18] Muller, M. G. et al., *Cancer* 2003, 97, 1681-1692.
[19] De Veld, D. C. et al., *J. Biomed. Opt.* 2004, 9, 940-950.
[20] Haka, A. S. et al., *Proc. Natl. Acad. Sci. U.S.A.* 2005, 102, 12371-12376.
[21] Kanter, E. M. et al., *J. Biophoton.* 2009, 2, 81-90.
[22] Liu, J. et al., *ACS Nano* 2010, 4, 2755-2765.
[23] Kanter, E. M. et al., *Am. J. Obstet. Gynecol.* 2009, 200, 512.e1-5.
[24] Ramanujam, N. et al., *Photochem. Photobiol.* 1996, 64, 720-735.
[25] Schomacker, K. T. et al., *Lasers Surg. Med.* 1992, 12, 63-78.
[26] Qian, X.; Peng et al., *Nat. Biotechnol.* 2008, 26, 83-90.
[27] Gao, X. et al., *Nat. Biotechnol.* 2004, 22, 969-976.
[28] Jain, R. K., *Annu. Rev. Biomed. Eng.* 1999, 1, 241-263.
[29] Minchinton, A. I. et al., *Nat. Rev. Cancer* 2006, 6, 583-592.
[30] Dreher, M. R. et al., *J. Natl. Cancer Inst.* 2006, 98, 335-344.
[31] Carrabba, M. M. et al., *Proc. SPIE* 1991, 1434, 127-134.
[32] Christesen, S. et al., *J. Appl. Spectrosc.* 1999, 53, 850-855.
[33] Angel, S. M. et al., *Proc. SPIE* 1991, 1534, 72, doi.10.1117/12.44232.
[34] Mishra A. et al., *Chem. Rev.* 2000, 100, 1973-2012.
[35] Sloane, H. J.; Bramston, R., *Appl. Spectrosc.* 1973, 27, 217-225.
[36] Li, S. D.; Huang, L., *Mol. Pharm.* 2008, 5, 496-504.
[37] Smith, A. M. et al., *Adv. Drug Delivery Rev.* 2008, 60, 1226-1240.
[38] Ott, P., *Pharmacol. Toxicol.* 1998, 83, 1-48.
[39] Parungo, C. P. et al., *Chest* 2005, 127, 1799-1804.
[40] Parungo, C. P. et al., *Ann. Surg. Oncol.* 2004, 11, 1085-1092.
[41] Sevick-Muraca, E. M. et al., *Radiology* 2008, 246, 734-741.

[42] Yamashita, S. I. et al., *J. Thorac. Cardiovasc. Surg.* 2010, in press.
[43] Matsumura, Y.; Maeda, H. *Cancer Res.* 1986, 46, 6387-6392.
[44] Barth, B. M. et al., *ACS Nano* 2010, 4, 1279-1287.
[45] Saxena, V. et al., *Int. J. Pharm.* 2006, 308, 200-204.
[46] Saxena, V. et al., *J. Photochem. Photobiol., B* 2004, 74, 29-38.
[47] Yaseen, M. A. et al., *Mol. Pharm.* 2009, 6, 1321-1332.
[48] Singhal, S. et al., *Annu. Rev. Med.* 2010, 61, 359-373.

We claim:

1. A system for intraoperatively providing anatomical guidance in a diagnostic or therapeutic procedure, comprising:
    (a) a lamp configured to emit a beam of visible light to an area of interest of a living subject;
    (b) a laser configured to emit a beam of near-infrared light to the area of interest;
    (c) a probe device configured to be held by hand optically coupled to the laser but not optically coupled to the lamp, comprising an optical fiber configured to deliver the emitted beam of near-infrared light to illuminate the area of interest and configured to collect light that is scattered or emitted from a contrast agent introduced into target tissues in the area of interest, in response to illumination by the laser;
    (d) a spectrometer optically coupled to the probe device and configured to detect the collected light and to generate a corresponding signal that comprises collected light data, and wherein the probe device is further configured to transmit the collected light to the spectrometer through the optical fiber of the probe device;
    (e) a first camera configured to detect visible light that is emitted from the area of interest in response to illumination by the lamp through an optical path that has no overlapping portion with the optical fiber of the probe device, and to generate a corresponding signal comprising visible light data;
    (f) a second camera configured to detect near-infrared light having a first predetermined wavelength that is emitted from the area of interest in response to illumination by the laser and to generate a corresponding signal comprising a first set of near-infrared light data;
    (g) a third camera configured to detect near-infrared light having a second predetermined wavelength that is different from the first predetermined wavelength and that is emitted from the area of interest in response to illumination by the laser, and to generate a corresponding signal comprising a second set of near-infrared light data;
    (h) a display for displaying at least one visual representation of data; and
    (i) a programmable processor in communication with each of the lamp, laser, spectrometer, first camera, second camera, third camera, and display, and programmed to generate at least one real-time integrated visual representation of the area of interest from each of the collected light data, visible light data, first set of near-infrared light data, and second set of near-infrared light data and to display the at least one real-time visual representation on the display, for guidance during the diagnostic or therapeutic procedure.

2. The system of claim 1, wherein the contrast agent comprises at least one of a Raman probe agent and a fluorescence probe agent and the collected light data comprises at least one of Raman data and fluorescence data, respectively.

3. The system of claim 2, wherein the at least one integrated visual representation comprises a wide-field image of the area of interest generated from the visible light data, a laser excitation image of a selected area of the area of interest defined within the wide-field image and generated from at least one of the generated first set of near-infrared light data and the generated second set of near-infrared light data, and at least one of a Raman image generated from the Raman data and a fluorescence image generated from the fluorescence data, wherein the at least one of the Raman image and fluorescence image is defined within the wide-field image and the laser excitation image.

4. The system of claim 3, wherein the at least one of the Raman image and the fluorescence image is an overlay image on the laser excitation image.

5. The system of claim 1, wherein each of the first, second, and third camera is a CCD camera.

6. An imaging system using integrated bright-field imaging, near-infrared imaging, and at least one of Raman imaging and fluorescence imaging for intraoperatively evaluating target tissues in an area of interest of a living subject, comprising:
    (a) a lamp for delivering a beam of visible light to the area of interest and a laser for delivering a beam of near-infrared light to the area of interest;
    (b) a Raman and fluorescence imaging device, comprising:
        (i) a probe device configured to be held by hand optically coupled to the laser but not optically coupled to the lamp, for delivering the near infrared light to illuminate target tissues of the area of interest and for collecting at least one of scattered light and emitted light from a corresponding at least one of a Raman probe agent and a fluorescence probe agent that is introduced into the target tissues and illuminated by the laser; and
        (ii) a spectrometer in optical communication with the probe device for obtaining at least one of Raman data from the collected scattered light and fluorescence data from the collected emitted light, respectively, transmitted through the probe device; and
    (c) a bright-field imaging system, comprising:
        (i) a first camera for obtaining visible light data from visible light emitted from the area of interest in response to illumination by the lamp, transmitted through an optical path that has no overlapping portion with the probe device;
        (ii) a second camera for obtaining a first set of near-infrared data from light having a first predetermined wavelength that is emitted from the area of interest in response to illumination by the laser; and
        (iii) a third camera for obtaining a second set of near infrared data from light having a second predetermined wavelength that is different from the first predetermined wavelength and that is emitted from the area of interest in response to illumination by the laser;
    further comprising an optical port, a system lens comprising a UV-NIR compact lens, a first achromatic correction lens, a first dichroic mirror, a second dichroic mirror, a neutral density filter, a bandpass filter, a longpass filter, a second achromatic lens, a third achromatic lens, and a fourth achromatic lens;

wherein the optical port and the first camera define a first optical path therebetween having the first dichroic mirror, the second dichroic mirror, and the second achromatic lens;

wherein the optical port and the second camera define a second optical path therebetween having the first dichroic mirror, the second dichroic mirror, the neutral density filter, and the third achromatic lens;

and wherein the optical port and the third camera define a third optical path therebetween having the first dichroic mirror, the longpass filter, the bandpass filter, and the fourth achromatic lens.

7. The imaging system of claim 6, further comprising:
(d) a display for displaying at least one visual representation of data; and
(e) a programmable processor in communication with each of the lamp, laser, spectrometer, first camera, second camera, third camera, and display, and programmed for generating in real time at least one integrated visual representation of the area of interest from the visible light data, first set of near-infrared data, second set of near-infrared data, and at least one of the Raman data and fluorescence data and displaying the integrated visual representation on the display, to provide guidance for performing a diagnostic or therapeutic procedure.

8. The imaging system of claim 7, wherein the at least one real-time integrated visual representation of the area of interest comprises a wide-field image of the area of interest generated from the visible light data, a laser excitation image of a predetermined area defined within the wide-field image that is generated from at least one of the first set of near-infrared data and the second set of near-infrared data, and at least one of a Raman image and a fluorescence image that is generated from a corresponding at least one of the Raman data and fluorescence data.

9. The imaging system of claim 8, wherein the laser excitation image is an overlay image on the wide-field image and represents the location of the delivered beam of near-infrared light within the area of interest.

10. The imaging system of claim 8, wherein the at least one of the Raman data and fluorescence data is represented by a signal that, when exceeding a predefined threshold level, signifies disease in the target tissues.

11. The imaging system of claim 10, wherein the at least one of the Raman image and the fluorescence image is a color overlay image on the laser excitation image, having an opacity representative of the level of the signal exceeding the predefined threshold level.

12. The imaging system of claim 11, wherein the opacity of the color overlay image decays over time to be progressively more translucent relative to the laser excitation image.

13. The imaging system of claim 6, wherein each of the first, second, and third camera is a CCD camera.

14. A method for intraoperatively providing anatomical guidance in a diagnostic or therapeutic procedure, comprising the steps of:
(a) introducing at least one contrast agent into target tissues in an area of interest of a living subject;
(b) emitting a beam of visible light to the area of interest, using a lamp;
(c) emitting a beam of near-infrared light to the area of interest, using a laser;
(d) delivering the emitted beam of near-infrared light to illuminate the area of interest, using an optical fiber of a probe device configured to be held by hand that is optically coupled to the laser but not optically coupled to the lamp;
(e) collecting at least one of scattered light and emitted light from the contrast agent in response to illumination by the laser, using the optical fiber of the probe device, wherein the contrast agent comprises at least one of a Raman probe agent and a fluorescence probe agent;
(f) detecting the collected light and generating a corresponding signal that comprises collected light data, using a spectrometer that is optically coupled to the optical fiber, and wherein the optical fiber is further configured to deliver the collected light to the spectrometer through the probe device;
(g) detecting visible light that is emitted from the area of interest in response to illumination by the lamp through an optical path that has no overlapping portion with the optical fiber of the probe device, and generating a corresponding signal comprising visible light data, using a first camera;
(h) detecting near-infrared light having a first predetermined wavelength that is emitted from the area of interest in response to illumination by the laser and generating a corresponding signal comprising a first set of near-infrared light data, using a second camera;
(i) detecting near-infrared light having a second predetermined wavelength that is different from the first predetermined wavelength and that is emitted from the area of interest in response to illumination by the laser and generating a corresponding signal comprising a second set of near-infrared light data, using a third camera;
(j) generating at least one real-time integrated visual representation of the area of interest from the collected light data, visible light data, first set of near-infrared data, and second set of near-infrared data, using a programmable processor in communication with each of the spectrometer, first camera, second camera, and third camera; and
(k) displaying the at least one real-time integrated visual representation generated by the programmable processor, for guidance during a diagnostic or therapeutic procedure, using a display in communication with the programmable processor.

15. The method of claim 14, wherein the step of generating the at least one real-time integrated visual representation of the area of interest comprises the steps of generating a wide-field image of the area of interest from the visible light data, generating a laser excitation image of a selected area of the area of interest defined within the wide-field image from at least one of the first set near-infrared light data and the second set of near-infrared light data, and generating at least one of a Raman image and a fluorescence image, from the collected light data, that is defined within the wide-field image and the laser excitation image.

16. The method of claim 14, wherein each of the first, second, and third camera is a CCD camera.

17. A non-transitory tangible computer-readable medium having stored thereon computer-executable instructions which, when executed by a programmable processor, cause a computer to perform functions for intraoperatively providing anatomical guidance in a surgical procedure, the functions comprising:
(a) causing a lamp in communication with the programmable processor to emit a beam of visible light to an area of interest of a living subject;

(b) causing a laser optically coupled to an optical fiber and in communication with the programmable processor to emit a beam of near-infrared light to the area of interest through the optical fiber, wherein the optical fiber is not optically coupled to the lamp;

(c) causing the optical fiber to collect at least one of light scattered from a Raman probe agent introduced into the target tissues in response to illumination by the laser and light emitted from fluorescence probe agent introduced into the target tissues in response to illumination by the laser;

(d) causing a spectrometer in communication with the programmable processor and the optical fiber to detect at least one of light that is scattered from the Raman probe agent and light that is emitted from the fluorescence probe agent, and collected through the optical fiber, in response to illumination from the second light source laser;

(e) causing the spectrometer to generate at least one of a signal from the detected scattered light that comprises Raman data and a signal from the detected emitted light that comprises fluorescence data, respectively;

(f) causing a first camera that is in communication with the programmable processor to detect visible light that is emitted from the area of interest in response to illumination by the lamp through an optical path that has no overlapping portion with the optical fiber, and causing the first camera to generate a corresponding signal comprising visible light data;

(g) causing a second camera that is in communication with the programmable processor to detect near-infrared light having a first predetermined wavelength that is emitted from the area of interest in response to illumination by the laser and causing the second camera to generate a corresponding signal comprising a first set of near-infrared light data;

(h) causing a third camera that is in communication with the programmable processor to detect near-infrared light having a second predetermined wavelength that is different from the first predetermined wavelength and that is emitted from the area of interest in response to illumination by the laser, and causing the third camera to generate a corresponding signal comprising a second set of near-infrared light data;

(i) generating at least one real-time integrated visual representation of the area of interest from the visible light data, first set of near-infrared data, second set of near-infrared data, and at least one of the Raman data and fluorescence data; and (j) causing a display in communication with the programmable processor to display the generated at least one real-time integrated visual representation for guidance during a diagnostic or therapeutic procedure.

18. The non-transitory tangible computer-readable medium of claim 17, wherein the step of generating the at least one real-time integrated visual representation of the area of interest comprises the steps of generating a wide-field image of the area of interest from the visible light data, generating a laser excitation image of a selected area of the area of interest defined within the wide-field image from at least one of the first set near-infrared light data and the second set of near-infrared light data, and generating at least one of a Raman image from the Raman data and a fluorescence image from the fluorescence data that is defined within the wide-field image and the laser excitation image.

19. The non-transitory tangible computer-readable medium of claim 18, wherein the at least one of the Raman image and the fluorescence image is an overlay image on the laser excitation image.

20. The non-transitory tangible computer-readable medium of claim 17, wherein each of the first, second, and third camera is a CCD camera.

21. A method for intraoperatively identifying disease in target tissues in an area of interest of a living subject, to be resected in a diagnostic or therapeutic procedure, comprising the steps of:

(a) introducing at least one of a Raman probe agent and a fluorescence probe agent into the area of interest until the at least one probe agents has accumulated in the target tissues;

(b) preparing the living subject and the area of interest for a diagnostic or therapeutic procedure;

(c) initializing an imaging system for integrated bright-field imaging, near-infrared imaging, and at least one of Raman imaging and fluorescence imaging;

(d) beginning the diagnostic or therapeutic procedure in the area of interest;

(e) using a first real-time integrated visual representation of the area of interest and the target tissues, generated by the imaging system, to identify a boundary of the target tissues that are diseased;

(f) performing a surgical resection of the identified diseased target tissues within the boundary;

(g) after the surgical resection, using a second displayed at least one real-time integrated visual representation of the area of interest and the target tissues, generated by the imaging system, to identify any remaining diseased target tissues within the boundary; and (h) if any remaining diseased target tissues are identified, performing a series of further surgical resections on identified remaining diseased target tissues corresponding to a respective series of real-time integrated visual representations generated by the imaging system, until the area of interest is free from diseased target tissues.

wherein the imaging system comprises:

(i) a lamp configured to emit a beam of visible light to an area of interest of a living subject;

(ii) a laser configured to emit a beam of near-infrared light to the area of interest;

(iii) a probe device configured to be held by hand optically coupled to the laser but not optically coupled to the lamp, comprising an optical fiber configured to deliver the emitted beam of near-infrared light to illuminate the area of interest and configured to collect light that is scattered or emitted from a contrast agent introduced into target tissues in the area of interest, in response to illumination by the laser;

(iv) a spectrometer optically coupled to the probe device and configured to detect the collected light and to generate a corresponding signal that comprises collected light data, and wherein the probe device is further configured to transmit the collected light to the spectrometer through the optical fiber of the probe device;

(v) a first camera configured to detect visible light that is emitted from the area of interest in response to illumination by the lamp through an optical path that has no overlapping portion with the optical fiber of the probe device, and to generate a corresponding signal comprising visible light data;

(vi) a second camera configured to detect near-infrared light having a first predetermined wavelength that is emitted from the area of interest in response to illumination by the laser and to generate a corresponding signal comprising a first set of near-infrared light data;

(vii) a third camera configured to detect near-infrared light having a second predetermined wavelength that is different from the first predetermined wavelength and that is emitted from the area of interest in response to illumination by the laser, and to generate a corresponding signal comprising a second set of near-infrared light data;

(viii) a display for displaying at least one visual representation of data; and (ix) a programmable processor in communication with each of the lamp, laser, spectrometer, first camera, second camera, third camera, and display, and programmed to generate at least one real-time integrated visual representation of the area of interest from each of the collected light data, visible light data, first set of near-infrared light data, and second set of near-infrared light data and to display the at least one real-time visual representation on the display, for guidance during the diagnostic or therapeutic procedure.

22. The method of claim 21, wherein the step of identifying the boundary of the target tissues that are diseased and the step of identifying any remaining diseased target tissues within the boundary comprise identifying visual representations of the first set of near-infrared light data, second set of near-infrared light data, and collected light data that are displayed in a selected area of the integrated visual representation.

23. The method of claim 21, wherein the visual representation of the first set of near-infrared data and second set of near-infrared data is a laser excitation image that represents the location of the delivered beam of near-infrared light within the area of interest, and that is displayed as a color overlay image on the wide-field image.

24. The method of claim 23, wherein the signal representing the collected light data that is generated by spectrometer, when exceeding a predetermined threshold level, signifies disease in the target tissues.

25. The method of claim 24, wherein the visual representation of the collected light data is a color overlay image on the laser excitation image, having an opacity representative of the level of the signal exceeding the predefined threshold level.

26. The method of claim 25, wherein the opacity of the color overlay image that represents the collected light data decays over time to be progressively more translucent relative to the laser excitation image.

27. The method of claim 21, wherein each of the first, second, and third camera is a CCD camera.

* * * * *

UNITED STATES PATENT AND TRADEMARK OFFICE
CERTIFICATE OF CORRECTION

PATENT NO.      : 9,451,882 B2
APPLICATION NO. : 14/086334
DATED           : September 27, 2016
INVENTOR(S)     : Nie et al.

Page 1 of 1

It is certified that error appears in the above-identified patent and that said Letters Patent is hereby corrected as shown below:

On the title page, item (56)
Page 2/other publications (col. 2, line 27), please change "Molecularimaging" to
-- Molecular imaging --
In the specification
Column 4, line 16, please change "near infrared" to -- near-infrared --
Column 4, line 40, please change "near infrared" to -- near-infrared --
Column 5, line 20, please change "at lest" to -- at least --
Column 10, line 46, please change "teens" to -- terms --
Column 11, line 35, please change "and is" to -- is --
Column 12, line 23, please change "and that" to -- that --
Column 13, line 17, please change "102b" to -- 126 --
Column 13, line 21, please change "126" to -- 122b --
Column 13, line 55, please change "146e" to -- 146c --
Column 15, line 61, please change "146e" to -- 146c --
Column 18, line 40, please change "subtrate" to -- substrate --
Column 21, line 47, please change "FIG 4A" to -- FIG 6A --
In the claims
Column 28, line 34 (claim 6, line 13), please change "near infrared" to -- near-infrared --
Column 32, line 30 (claim 21, line 22), please change "displayed" to -- display --
Column 34, line 14 (claim 24, line 2), please change "by" to -- by the --

Signed and Sealed this
Twentieth Day of December, 2016

Michelle K. Lee
*Director of the United States Patent and Trademark Office*